US012311343B2

(12) United States Patent
Notestein et al.

(10) Patent No.: US 12,311,343 B2
(45) Date of Patent: May 27, 2025

(54) TANDEM CATALYSIS FOR ALKANE AND ALCOHOL DEHYDROGENATION COUPLED TO SELECTIVE HYDROGEN COMBUSTION

(71) Applicant: Northwestern University, Evanston, IL (US)

(72) Inventors: Justin M. Notestein, Evanston, IL (US); Peter C. Stair, Santa Fe, NM (US); Huan Yan, Evanston, IL (US)

(73) Assignee: Northwestern University, Evanston, IL (US)

( * ) Notice: Subject to any disclaimer, the term of this patent is extended or adjusted under 35 U.S.C. 154(b) by 130 days.

(21) Appl. No.: 17/927,200

(22) PCT Filed: Jul. 29, 2021

(86) PCT No.: PCT/US2021/043601
§ 371 (c)(1),
(2) Date: Nov. 22, 2022

(87) PCT Pub. No.: WO2022/031501
PCT Pub. Date: Feb. 10, 2022

(65) Prior Publication Data
US 2023/0241586 A1      Aug. 3, 2023

Related U.S. Application Data

(60) Provisional application No. 63/060,308, filed on Aug. 3, 2020.

(51) Int. Cl.
*B01J 23/42*      (2006.01)
*B01J 21/04*      (2006.01)
(Continued)

(52) U.S. Cl.
CPC ............... *B01J 23/42* (2013.01); *B01J 21/04* (2013.01); *B01J 23/08* (2013.01); *B01J 35/23* (2024.01);
(Continued)

(58) Field of Classification Search
CPC ... B01J 23/42; B01J 21/04; B01J 23/08; B01J 35/23; B01J 35/393; B01J 37/0221;
(Continued)

(56) References Cited

U.S. PATENT DOCUMENTS 10,828,621 B2 * 11/2020 Bunquin ................. B01J 37/024
2017/0333878 A1    11/2017 Stair et al.
2018/0093253 A1 *  4/2018 Bunquin ................. C07C 5/3337

FOREIGN PATENT DOCUMENTS

WO    WO 2012/166514 A1    12/2012
WO    WO 2018/232133 A1    12/2018
(Continued)

OTHER PUBLICATIONS

Lu, Junling, Jeffrey W. Elam, and Peter C. Stair. "Synthesis and stabilization of supported metal catalysts by atomic layer deposition." *Accounts of chemical research* 46.8 (2013): 1806-1815.
(Continued)

*Primary Examiner* — Prem C Singh
*Assistant Examiner* — Francis C Campanell
(74) *Attorney, Agent, or Firm* — BELL & MANNING, LLC

(57) ABSTRACT

Tandem catalysts for the dehydrogenation of alkanes and/or alcohols in tandem with selective hydrogen combustion are provided. Also provided are methods of making the catalysts and methods of using the catalysis for the dehydrogenation of alkanes and/or alcohols. The catalysts include a support having a surface, dehydrogenation catalysts particles dispersed on the surface of the support, and a porous selective
(Continued)

hydrogen combustion catalyst overcoat on the dehydration catalyst particles. The catalysts couple dehydrogenation with selective hydrogen combustion in a sequence of reactions occurring in tandem to shift the equilibrium of the dehydrogenation towards higher conversion.

21 Claims, 19 Drawing Sheets

(51) Int. Cl.
    *B01J 23/08*     (2006.01)
    *B01J 35/23*     (2024.01)
    *B01J 35/30*     (2024.01)
    *B01J 37/02*     (2006.01)
    *C07C 5/333*     (2006.01)

(52) U.S. Cl.
    CPC ......... *B01J 35/393* (2024.01); *B01J 37/0221* (2013.01); *B01J 37/0228* (2013.01); *B01J 37/0244* (2013.01); *C07C 5/3337* (2013.01); *C07C 2521/04* (2013.01); *C07C 2523/08* (2013.01); *C07C 2523/42* (2013.01)

(58) Field of Classification Search
    CPC .... B01J 37/0228; B01J 37/0244; B01J 23/62; B01J 37/0225; C07C 5/3337; C07C 2521/04; C07C 2523/08; C07C 2523/42
    USPC .......................................................... 585/660
    See application file for complete search history.

(56) References Cited

FOREIGN PATENT DOCUMENTS

WO     WO 2020/046978 A1     3/2020
WO     WO 2021/025938 A1     2/2021

OTHER PUBLICATIONS

Tsikoyiannis, John G., David L. Stern, and Robert K. Grasselli. "Metal oxides as selective hydrogen combustion (SHC) catalysts and their potential in light paraffin dehydrogenation." *Journal of Catalysis* 184.1 (1999): 77-86.

Liu, Yunling, et al. "Assembly of metal-organic frameworks (MOFs) based on indium-trimer building blocks: a porous MOF with soc topology and high hydrogen storage." *Angewandte Chemie* 119.18 (2007): 3342-3347.

Sattler, Jesper JHB, et al. "Catalytic dehydrogenation of light alkanes on metals and metal oxides." *Chemical reviews* 114.20 (2014): 10613-10653.

Van der Zande, L. M., E. A. De Graaf, and Gadi Rothenberg. "Design and parallel synthesis of novel selective hydrogen oxidation catalysts and their application in alkane dehydrogenation." *Advanced Synthesis & Catalysis* 344.8 (2002): 884-889.

The International Search Report and Written Opinion issued on Dec. 30, 2021 for international patent application No. PCT/US21/43601; pp. 1-11.

Junling Lu et al., "Coking- and Sintering-Resistant Palladium Catalysts Achieved Through Atomic Layer Deposition," *Science* Mar. 9, 2012, vol. 335; pp. 1205-1208.

Chen, Sai, et al. "Propane dehydrogenation: catalyst development, new chemistry, and emerging technologies." *Chemical Society Reviews* 50.5 (2021): 3315-3354.

Stefan Vajda et al., "Subnanometre platinum clusters as highly active and selective catalysts for the oxidative dehydrogenation of propane," *Nature Materials*—Advance Online Publication Mar. 2009; pp. 1-28.

Izabela A. Samek et al., "Structure and Activity of Mixed VOx—CeO2 Domains Supported on Alumina in Cyclohexane Oxidative Dehydrogenation," Manuscript published by Elsevier 2020; pp. 1-41. Version of Record: https://www.sciencedirect.com/science/article/pii/S0021951720300634Manuscript_0b0002a2267c44e2d4d1207f773faeb6.

* cited by examiner

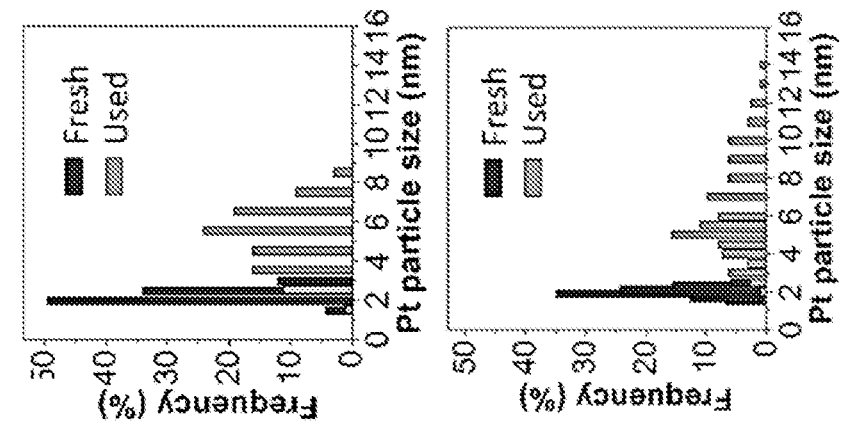
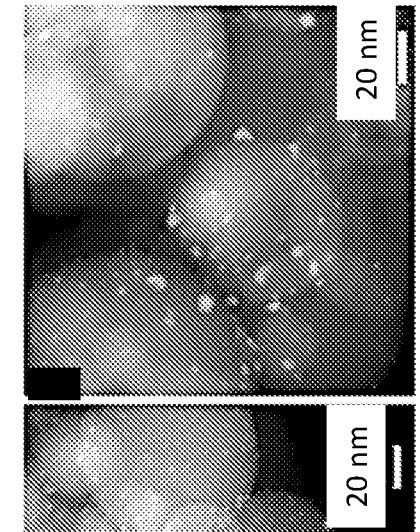
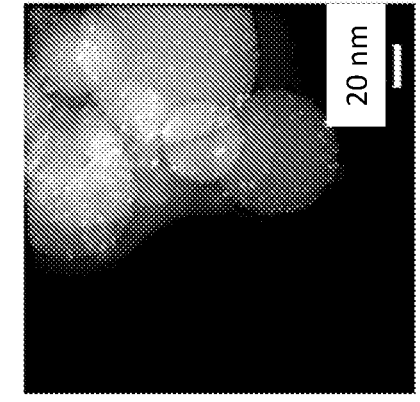
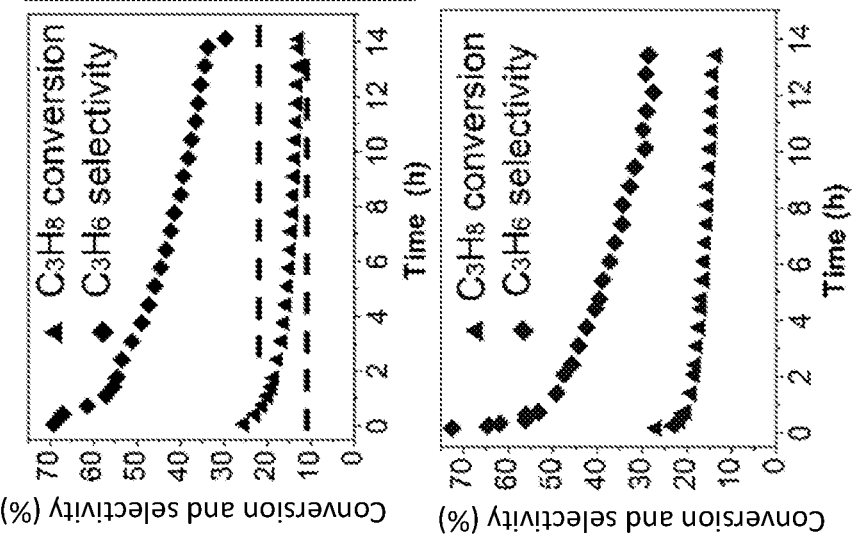

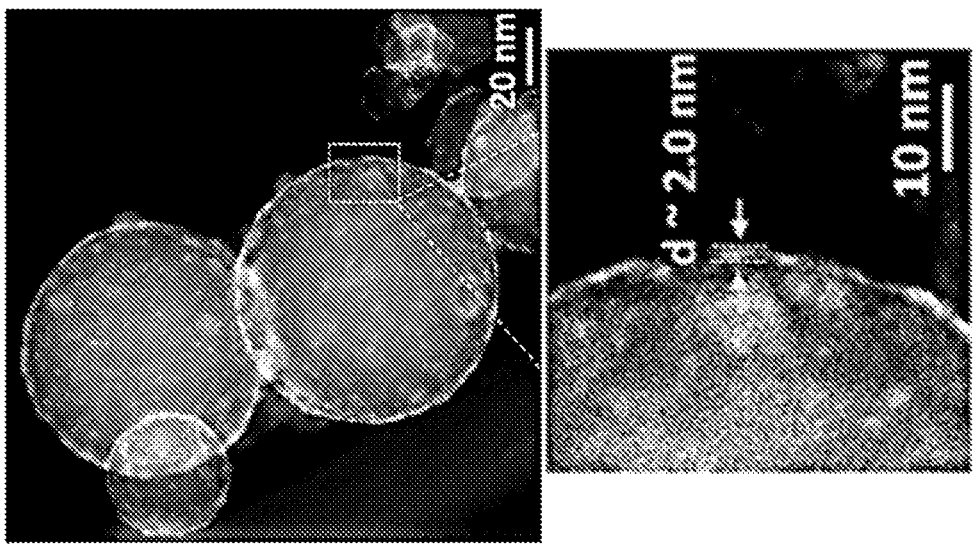
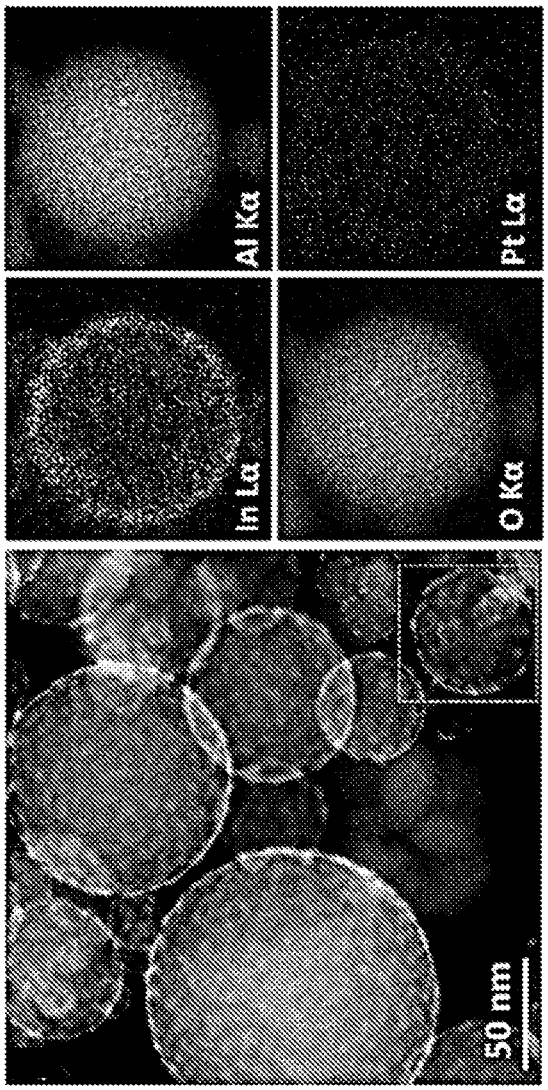
FIG. 17A
FIG. 17B

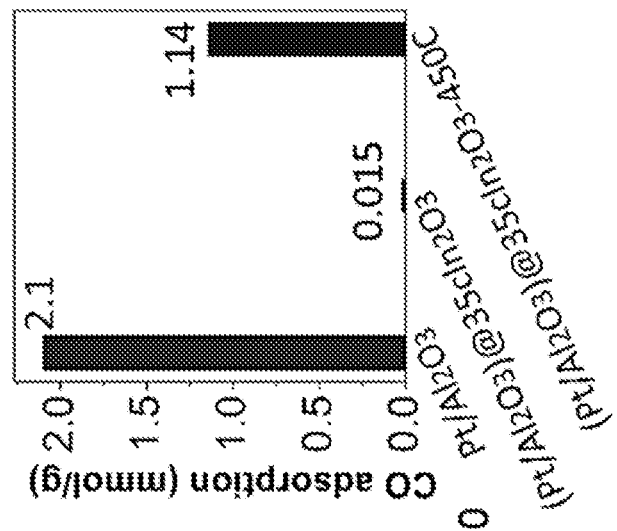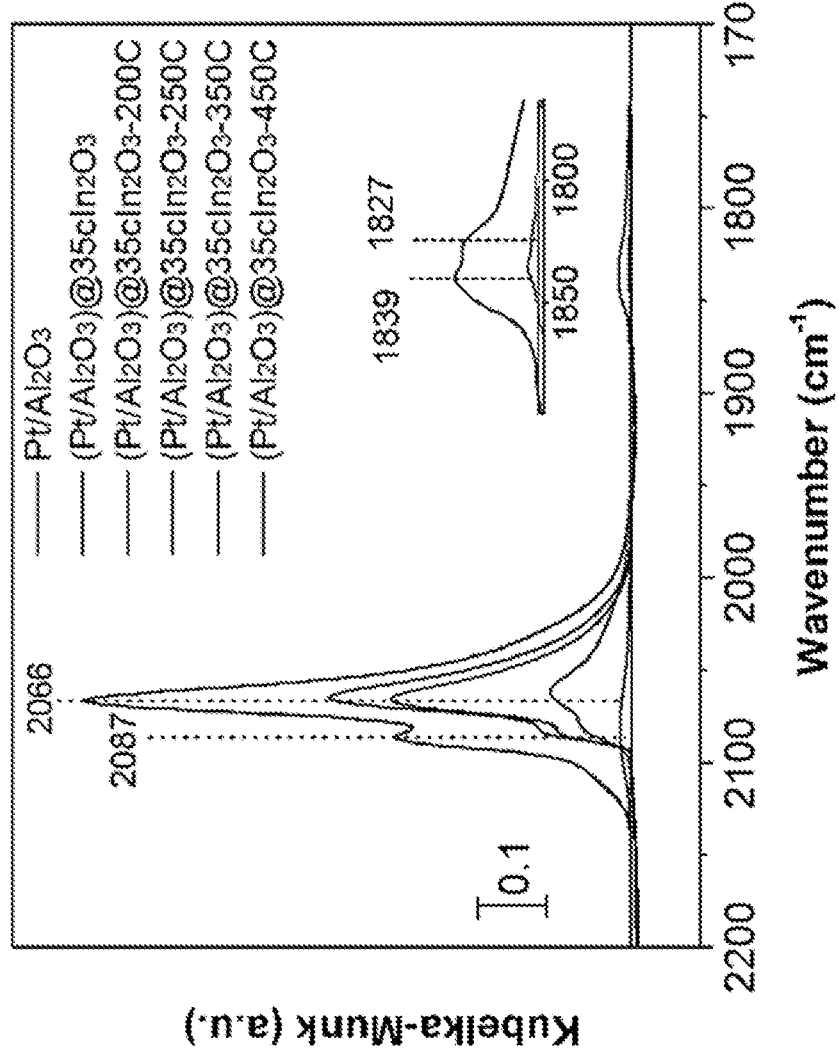
FIG. 17C
FIG. 17D

US 12,311,343 B2

TANDEM CATALYSIS FOR ALKANE AND ALCOHOL DEHYDROGENATION COUPLED TO SELECTIVE HYDROGEN COMBUSTION

CROSS-REFERENCE TO RELATED APPLICATIONS

The present application is a National Stage of International Application No. PCT/US21/43601, filed Jul. 29, 2021, which claims priority to U.S. provisional patent application No. 63/060,308 that was filed Aug. 3, 2020, the entire contents of both of which are incorporated herein by reference.

REFERENCE TO GOVERNMENT RIGHTS

This invention was made with government support under 1647722 awarded by the National Science Foundation. The government has certain rights in the invention.

BACKGROUND

The catalytic dehydrogenation of alkanes, such as propane to propylene, is of great interest due to the essential role of olefin intermediates in industrial processes and because of a gap between supply and anticipated demand. Propylene is an essential chemical intermediate, and demand is expected to outstrip supply for the immediate future. Dehydrogenation of propane is endothermic and equilibrium limited, necessitating high temperatures and/or complex multi-reactor schemes with sequences of dehydrogenation and selective $H_2$ combustion in series. Oxidative dehydrogenation of propane (ODHP) has long been proposed as a solution to overcoming the thermodynamic limitations of non-oxidative propane dehydrogenation (PDH), but after decades of research, per-pass yields remain low due to poor selectivity at high conversion.

ODHP catalysts reported to date all suffer from decreasing selectivity as conversion increases because the allylic C—H bond of propylene is weaker than the C—H bond of propane. This an intrinsic property of any oxidant strong enough to oxidize hydrocarbons. For instance, the most investigated vanadium-based catalysts achieve only ~17% propane yield (60% selectivity at ~28% propane conversion) due to the over-oxidation of the propylene product. Another promising catalyst, boron nitride (BN) offers only ~15% propylene yield (75% propylene selectivity at less than 20% propane conversion). Decades of effort have unsuccessfully sought ODHP catalysts for high yields of propylene.

SUMMARY

Tandem catalysts, methods for using the tandem catalysts for the dehydrogenation of alkanes or alcohols, and methods of making the tandem catalysts are provided.

One example of a tandem catalyst includes: a support having a surface; catalyst particles dispersed on the surface of the support, the catalyst particles comprising a material that is catalytically active for dehydrogenation of an alkane or an alcohol; and a catalytic porous overcoat on the catalyst particles, the porous overcoat comprising a material that is catalytically active for selective hydrogen combustion in the presence of the alkane or the alcohol.

One embodiment of a method from the dehydrogenation of an alkane or alcohol includes the steps of: exposing the alkane or the alcohol to a catalyst in the presence of oxygen, whereby the alkane or the alcohol is dehydrogenated to form a dehydrogenation product. The catalyst includes a support having a surface; catalyst particles dispersed on the surface of the support, the catalyst particles comprising a material that is catalytically active for the dehydrogenation of the alkane or the alcohol; and a catalytic porous overcoat on the catalyst particles, the porous overcoat comprising a material that is catalytically active for selective hydrogen combustion in the presence of the alkane or the alcohol.

One embodiment of making a catalyst includes the steps of: providing a support having a surface and a plurality of catalyst particles dispersed on the surface, the catalyst particles comprising a material that is catalytically active for the dehydrogenation of an alkane or an alcohol; and overcoating the catalyst particles with a porous overcoat comprising a material that is catalytically active for selective hydrogen combustion in the presence of the alkane or the alcohol.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIGS. 2A-2L show propane conversion (▲) and propylene selectivity (♦) of a tandem PDH-SHC reaction (FIGS. 2A, 2E, 2I) over model catalysts $Pt/Al_2O_3+Al_2O_3@In_2O_3$ (FIGS. 2A-2D), $Pt/(Al_2O_3@35cIn_2O_3)$ (FIGS. 2E-2H), and $(Pt/Al_2O_3)@35cIn_2O_3$, (FIGS. 2I-2L). T=450° C., $P_{C3H8}$:$P_{O2}$:$P_{N2}$=10:5:85 kPa. $WHSV^{-1}$=1.55 $kg_{C3H8}^{-1}$ $kg_{catalyst}$ h for $(Pt/Al_2O_3)@35cIn_2O_3$ and $Pt/(Al_2O_3@35cIn_2O_3)$, and 3.1 $kg_{C3H8}^{-1}$ $kg_{catalyst}$ h for $Pt/Al_2O_3+Al_2O_3@In_2O_3$. Dashed lines show the propane conversion and propylene selectivity of $Pt/Al_2O_3$ alone. STEM images are shown of fresh (FIGS. 2B, 2F, 2J) and used (FIGS. 2C, 2G, 2K) catalysts after 14 hours on stream. Pt particle size distributions (FIGS. 2D, 2H, 2L) of fresh and used catalysts are shown.

FIG. 5A shows propane conversion, propylene selectivity and carbon balance vs. reaction time on stream. FIG. 5B shows outlet Hz/propylene ratio vs. reaction time on stream. T=450° C., propane: O$_2$=2:1, WHSV$^{-1}$=3.1 kg$_{C3H8}^{-1}$ kg$_{catalyst}$ h.

FIG. 11A shows propane conversion vs. reaction time on stream. FIG. 11B shows propylene selectivity and outlet Hz/propylene ratio vs. reaction time on stream. T=450° C., P$_{C3H8}$:P$_{O2}$:P$_{N2}$=10:5:85 kPa (no O$_2$ in shaded region), WHSV$^{-1}$=3.1 kg$_{C3H8}^{-1}$ kg$_{catalyst}$ h.

FIG. 15A shows the ratio of H$_2$ to propylene as a function of reaction time on stream. FIG. 15B shows propane conversion and propylene selectivity as a function of reaction time on stream. T=450° C., P$_{C3H8}$:P$_{O2}$:P$_{N2}$=10:5:85 kPa, WHSV$^{-1}$=1.55 kg$_{C3H8}^{-1}$ kg$_{catalyst}$ h. The H$_2$ to propylene ratio is similar to the value for the uncoated Pt/Al$_2$O$_3$. As compared to Pt/Al$_2$O$_3$, the (Pt/Al$_2$O$_3$)@35 cAl$_2$O$_3$ catalyst showed a lower, but more stable propane conversion, and a higher and more stable propylene selectivity.

FIG. 16A shows the ratio of H$_2$ to propylene as a function of reaction time on stream. FIG. 16B shows propane conversion and propylene selectivity as a function of reaction time on stream. T=450° C., P$_{C3H8}$:P$_{O2}$:P$_{N2}$=10:5:85 kPa, WHSV$^{-1}$=3.1 kg$_{C3H8}^{-1}$ kg$_{catalyst}$ h. Although the H$_2$ to propylene ratio decreases only slightly from 0.85 to 0.80, the propylene selectivity decreases continuously. As compared to the optimal catalyst, Oxygen is not removed from Pt surface by a rapid nearby hydrogen combustion, resulting in more propylene and propane combustion.

FIGS. 17A-17D shows characterization of (Pt/Al$_2$O$_3$)@35cIn$_2$O$_3$ (optimum catalyst) and Pt/Al$_2$O$_3$ reference. FIGS. 17A-17B show scanning transmission electron microscopy (STEM) images of the tandem catalyst at low magnification and (FIG. 17A) selected area energy-dispersive X-ray spectroscopy elemental analysis (EDS)-mapping or (FIG. 17B) high magnification STEM image. FIG. 17C shows IR spectra of adsorbed CO on Pt/Al$_2$O$_3$ and the optimum catalyst after different temperature thermal pretreatments. Inset shows lower wavenumber region. FIG. 17D shows CO pulse chemisorption on Pt/Al$_2$O$_3$, fresh optimum catalyst and optimum catalyst after 450° C. thermal pretreatments in inert gas.

DETAILED DESCRIPTION

Catalysts for the dehydrogenation of alkanes and/or alcohols in tandem with selective hydrogen combustion are provided. Also provided are methods of making the catalysts and methods of using the catalysts for the dehydrogenation of alkanes and/or alcohols.

The catalysts include a coating of a selective hydrogen combustion catalyst over nanoscale particles of a dehydrogenation catalyst. While the dehydrogenation of alkanes and alcohols is typically limited by the reaction equilibrium at reasonable temperatures, the catalyst design described herein allows selective hydrogen combustion to pull the alkane and/or alcohol dehydrogenation reaction equilibrium forward, while hindering or preventing ambient oxygen from reacting on the dehydrogenation catalyst, which would lead to reduced product selectivity due to product combustion. As a result, the catalysts are able to provide high per-pass product yields.

The dehydrogenation reactions that can be carried out using the present catalysts include reactions of enormous economic importance. The tandem nature of the catalysts allows two or more reactions to be carried out in a single reactor using two or more catalysts, where each catalyst has no deleterious interactions with the other catalysts or reactants. This is an extremely demanding set of requirements, particularly, when oxidant co-feeds are used, because such co-feeds tend to exclude the possibility of multiple types of reactions occurring in the same reactor. For example, combining a selective hydrogen combustion catalyst with a separate selective propane dehydrogenation catalyst in a single reactor does not work because propane dehydration catalysts give very poor selectivity when exposed to oxidizing atmospheres. In contrast, the tandem catalyst design described herein spatially organizes the catalysts at the nanoscale to minimize the undesired oxidation reaction that could occur on the dehydrogenation catalyst.

Figure 1:
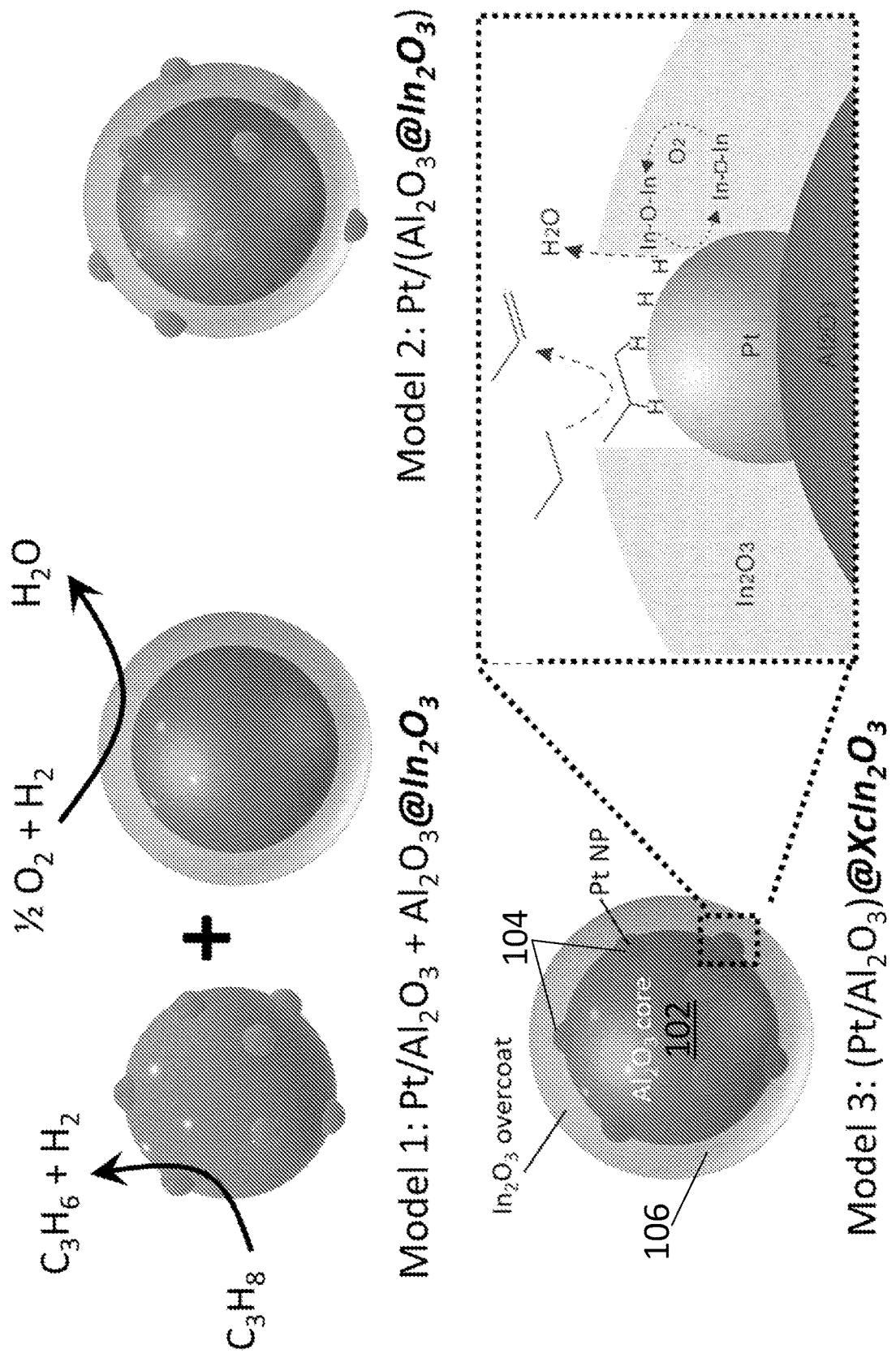
FIG. 1 shows three tandem catalyst models comprising a microporous $In_2O_3$ selective $H_2$ combustion catalyst and a $Pt/Al_2O_3$ propane dehydrogenation catalyst (Pt nanoparticles) on a support ($Al_2O_3$ particle). Tandem catalyst model 3, $(Pt/Al_2O_3)@35cIn_2O_3$ (35 cycles of $In_2O_3$ deposition), possess a ~2 nm $In_2O_3$ overcoat and 2.0-2.3 nm Pt nanoparticles. (An X is used to indicate that different numbers of cycles can be used to form the overcoat.) A tandem PDH-SHC reaction scheme for $(Pt/Al_2O_3)@35cIn_2O_3$ is shown in the lower right panel, wherein an alkane reactant accesses the dehydrogenation particle surface through a pore in the overcoat.

The basic structure of the tandem catalysts is shown schematically in FIG. 1, bottom panels. The catalysts include a support 102, dehydrogenation catalysts particles 104 dispersed on the surface of support 102, and a porous selective hydrogen combustion catalyst overcoat 106 on dehydration catalyst particles 104. In the example of FIG. 1, support 102 is $Al_2O_3$, dehydration catalyst particles 104 are platinum (Pt) nanoparticles, and porous overcoat 106 is an $In_2O_3$ coating. However, these particular materials are used for illustrative purposes only.

The support, which provides a high surface area to allow for a high dehydrogenation catalyst particle loading, can take on a variety of forms, including a powder, a porous film, and/or a porous membrane. The support may be, but need not be, porous. When the support is composed of a solid powder, the particles making up the powder may be much larger than (e.g., at least five times larger or at least ten times larger) the dehydrogenation catalyst particles. By way of illustration powder particles having an average size (diameter) in the range from 40 nm to 400 nm can be used. However, powder particles having an average particle size outside of this range can also be used. Moreover, micro and/or nanocrystalline powder particles can be used. Optionally, the powder particles can be sintered or otherwise fused or bonded together. The support may also comprise a film, such as a washcoat, of the powder particles on a supporting substrate.

The support material should be thermally stable against decomposition, phase transformations, and aggregation at the temperature at which the tandem dehydrogenation and hydrogen combustion are carried out. The support may be, but need not be, catalytically inert with respect to the dehydrogenation and hydrogen combustion reactions. Oxide support materials and non-oxide support materials can be used. Suitable oxide support materials include aluminum oxide, including magnesium- and zinc-doped aluminum oxide, zirconium oxide, magnesium oxide, titanium oxide, and silicon oxide.

The dehydrogenation catalyst particles are comprised of a material that is catalytically active for the dehydrogenation of an alkane or an alcohol at a dehydrogenation temperature or range of dehydrogenation temperatures. The dehydrogenation catalyst particles may include more than one type of particle in order to carry out the dehydrogenation of two or more different alkanes and/or alcohols. Depending on the dehydrogenation catalyst selected, a variety of starting alkanes can be converted into a variety of dehydrogenation products, including aliphatic or aromatic alkenes and cycloalkanes. For example, the catalysts can be used to convert ethane to ethylene, methane to ethylene, propane to propylene, butane to butene or butadiene, and/or paraffins to olefins. The dehydrogenation catalysts can also be selected for the conversion of alcohols to aldehydes, ketones, and/or esters. For example, the catalysts can be used to convert ethanol to ethyl acetate or 1,4 propane diol to butyrolactone.

Examples of materials that are catalytically active for the dehydrogenation of alkanes and/or alcohols include certain metals, such as platinum, nickel, cobalt, and iron. Other examples include platinum alloys, such as Pt—Sn, Pt—Zn, and Pt—In, certain oxides, such as iron oxide, chromium oxide, vanadium oxide, molybdenum oxide, and gallium oxide, carbides, such as molybdenum carbide, and sulfides, such as molybdenum sulfide, nickel sulfide, and cobalt sulfide.

The catalyst particles may have a variety of shapes and sizes. For example, nanoscale particles having an average size that is typically less than 10 nm can be used. This includes catalyst particles having an average size of less than 5 nm and further includes catalyst particles having an average size of 2 nm or less. By way of illustration, catalyst particles having an average size in the range from 1 nm to 10 nm can be used. However, larger particles are also suitable. The catalyst particles can be formed on the surface of the support substrate using, for example atomic layer deposition (ALD) growth, as illustrated in the Example. However, other methods can be used and the catalyst particles need not be formed in situ on the support; they can be pre-formed and later coated onto the support substrate. By way of illustration, particle coating techniques such as impregnation, exchange, grafting, and deposition-precipitation can be used. The dehydrogenation catalyst particle loading will depend on the particular dehydrogenation catalyst material being used and the catalysis process requirements. Generally, however, dehydrogenation catalyst loadings in the range from about 0.5 weight percent (wt. %) to about 10 wt. %, based on the total weight of the support and the dehydrogenation catalyst particles, are sufficient.

Once the dehydrogenation catalyst particles are dispersed on the support, a porous overcoat comprising a material that is catalytically active for hydrogen combustion at a hydrogen combustion temperature or range of hydrogen combustion temperatures is applied over the dispersed dehydrogenation catalyst particles. The material that is catalytically active for hydrogen combustion is selective for the combustion of hydrogen over the combustion of the alkane and/or alcohol being dehydrogenated. In addition to catalyzing combustion, the overcoat can stabilize the dehydrogenation catalyst particles against deactivation by sintering.

The porous overcoat can be applied on the dehydrogenation catalyst particles using, for example, ALD followed by a thermal treatment. However, other methods for growing or depositing porous films of a selective hydrogen combustion catalyst material can be used. Examples of selective hydrogen combustion catalysts include certain metal oxides, such as indium oxide, bismuth oxide, tungsten oxide, molybdenum oxide, nickel oxide, iron oxide, cobalt oxide, mixed oxides of molybdenum oxide, including with bismuth, indium, aluminum, iron, and lanthanum. perovskite oxides based on manganese, such as $SrMnO_3$, $CaMnO_3$, and $Mg_6MnO_8$. Some materials that are catalytically active for the dehydrogenation of one or more alkanes or alcohols may also be catalytically active for the selective combustion of hydrogen in the presence of one or more alkanes or alcohols.

Therefore, for purposes of clarification the material that is catalytically active for the dehydrogenation of an alkane and/or alcohol and the material that is catalytically active for the selective combustion of hydrogen in the tandem catalysts described herein are two different materials. To the extent that the selective hydrogen combustion catalyst is also able to catalyze the dehydrogenation of the alkane and/or alcohol, the primary reaction being catalyzed by the selective hydrogen combustion catalyst is the selective combustion of hydrogen. Similarly, to the extent that the dehydrogenation catalyst is also able to catalyze the combustion of alcohol the primary reaction being catalyzed by the dehydrogenation catalyst is the alkane and/or alcohol dehydrogenation.

The porous overcoat has a thickness and microporosity that enables access of the alkane and/or alcohol reactants to the underlying dehydrogenation catalyst particles. A thick overcoat may effectively render the underlying dehydrogenation catalyst particles inaccessible to the alkane and/or alcohols reactants. The optimal thickness and porosity will depend on the particular catalysis being carried out. Generally, overcoats with thicknesses in the range from about 1 nm to about 5 nm that include micropores having porosities that leave 10% to 90% of the dehydrogenation sites accessible are suitable.

The tandem catalysts can be used to dehydrogenate one or more alkanes and/or one or more alcohols by exposing the tandem catalysts to an environment that contains the one or more alkanes and/or one or more alcohols in the presence of oxygen at a temperature and for a period of time sufficient to facilitate the catalytic dehydrogenation reactions. The temperature at which the catalysis is carried out will depend on the particular catalysts and alkanes and/or alcohols being used, but typically temperatures in the range from about 300° C. to about 800° C., including in the range from 400° C. to 600° C., are suitable. For some dehydrogenation reactions, particularly alcohol dehydrogenations, lower temperatures, including temperatures at or near room temperature (23° C.) can be used.

During the tandem catalysis, alkane and/or alcohol dehydrogenation occurs on the surface of the dehydrogenation catalyst particles, while the $H_2$ that is formed as a product of the dehydrogenation is captured and converted to $H_2O$ in the presence of $O_2$ by the hydrogen combustion catalyst overcoat. This eliminates the need for selective membrane reactors to remove the hydrogen as it is generated. The presence of $O_2$ maintains the hydrogen combustion catalyst in an oxide state and hinders or prevents the reaction of the hydrogen combustion catalyst with the dehydrogenation catalyst to form a metal alloy. The heat provided by the hydrogen combustion and the consumption of the $H_2$ by the selective hydrogen combustion pulls the dehydrogenation reaction forward, and the layered geometry results in the preferential consumption of $O_2$ by the selective hydrogen combustion reaction, rather than the underlying dehydration catalyst sites, which would otherwise lead to extensive alkane, alcohol, and alkene combustion. Thus, by coupling dehydrogenation with selective hydrogen combustion in a sequence of reactions occurring in tandem in a single reactor, the equilibrium of the dehydrogenation is shifted towards higher conversion and selectivity. As a result, per pass product yields for oxidative dehydrogenation of greater than 30 percent can be achieved, including per pass yields of 35 percent or higher, with time-stable selectivity.

EXAMPLE

This example illustrates a fundamentally different approach to ODHP, utilizing a tandem catalyst based on Pt/$Al_2O_3$, an effective PDH catalyst, and an $In_2O_3$ film, a selective hydrogen combustion (SHC) catalyst that shifts the PDH equilibrium toward propylene. Three tandem catalyst designs (FIG. 1) were examined: A physical mixture of the two catalysts, Pt supported on an $In_2O_3$ film, and a layered geometry, were prepared by overcoating Pt/$Al_2O_3$ with an $In_2O_3$ film. The $In_2O_3$ films were produced by ALD. The performance of the layered geometry was vastly superior to both the other designs and to previously-reported ODHP catalysts. The $In_2O_3$ overcoat consumed $O_2$ before it reached the underlying Pt/$Al_2O_3$, where it would otherwise be detrimental to selectivity. The $In_2O_3$ also helped stabilize the Pt/$Al_2O_3$ against sintering. This nanoscale tandem catalyst design gave stable operation with up to 76% selectivity at 40% conversion for an overall 30% yield.

Here, a different approach was taken where tandem catalyst systems were created, composed of propane dehydrogenation (PDH) sites, provided by alumina-supported Pt nanoparticles (Pt/$Al_2O_3$) and selective $H_2$ combustion (SHC) sites, provided by an $In_2O_3$ thin film (FIG. 1). Three designs were investigated with progressively more intimate contact between the catalytic materials, as determined by the location of the $In_2O_3$ film: 1) a physical mixture of Pt/$Al_2O_3$ and $In_2O_3$-coated alumina powders (designated Pt/$Al_2O_3$+ $Al_2O_3$@$In_2O_3$); 2) Pt supported on an $In_2O_3$ film (designated Pt/($Al_2O_3$@$In_2O_3$)); and 3) Pt/$Al_2O_3$ coated by a porous $In_2O_3$ film to form a layered structure (designated (Pt/$Al_2O_3$)@$In_2O_3$). With Pt supported by $In_2O_3$ in the second design, the two materials were brought into contact to enhance the coupling of the two functions. In the third design, coating the Pt with $In_2O_3$ achieved an even more intimate contact.

The Pt nanoparticles (NPs) were synthesized by ALD on $Al_2O_3$(NanoDur) or $In_2O_3$-coated $Al_2O_3$ using a single cycle of trimethyl(methylcyclopentadienyl) platinum and $O_3$, although other routes could likely be used. $In_2O_3$ films of variable thickness were synthesized by 2-55 cycles of $In_2O_3$ ALD alternating cyclopentadienyl indium (InCp) and $O_3$, corresponding to 0.22-15.4 wt. % indium. Most of the catalytic experiments were performed using materials with 35 cycles of $In_2O_3$ ALD, designated 35c$In_2O_3$, containing 7 wt. % indium (Table 1).

TABLE 1

Indium weight loadings corresponding to different numbers of indium oxide ALD cycles.

| Indium ALD cycles | Indium loading (wt. %) |
|---|---|
| 0 | 0 |
| 2 | 0.22 |
| 10 | 2.78 |
| 15 | 4.24 |
| 20 | 5.76 |
| 35 | 7.04 |
| 55 | 15.4 |

The performance of the three designs under reaction conditions of 450° C. and $P_{C3H8}$:$P_{O2}$:$P_{N2}$=10:5:85 kPa, is summarized in FIGS. 2A-2L. The first design, a physical mixture of Pt/$Al_2O_3$ and $Al_2O_3$@$In_2O_3$, exhibited considerable propane conversion (25%), propylene selectivity (69%), and propylene yield (17%), at the start of reaction. However, the activity and selectivity dropped dramatically after 1 hour time on stream (TOS, FIG. 2A), approaching those of Pt/$Al_2O_3$ alone. For the physical mixture, the Pt sites catalyzed propane combustion in addition to PDH, resulting in low propylene selectivity, especially after the first hour.

The stoichiometric H₂/propylene ratio from PDH is 1 (FIG. 3), and the observed H₂/propylene ratio of 0.82 was less than the stoichiometric ratio for this design (FIG. 4), indicating that the $Al_2O_3$@$In_2O_3$ particles carried out SHC to some extent. In this design, the decrease in activity and propylene selectivity was at least partially a consequence of Pt NP aggregation (FIGS. 2B-2D). The fresh catalyst had a Pt particle size of 2.3±0.7 nm, whereas after 14 hours TOS at 450° C., the Pt NPs exhibited a broad particle size distribution (5.0±3.3 nm) characteristic of aggregation.

Figure 4:
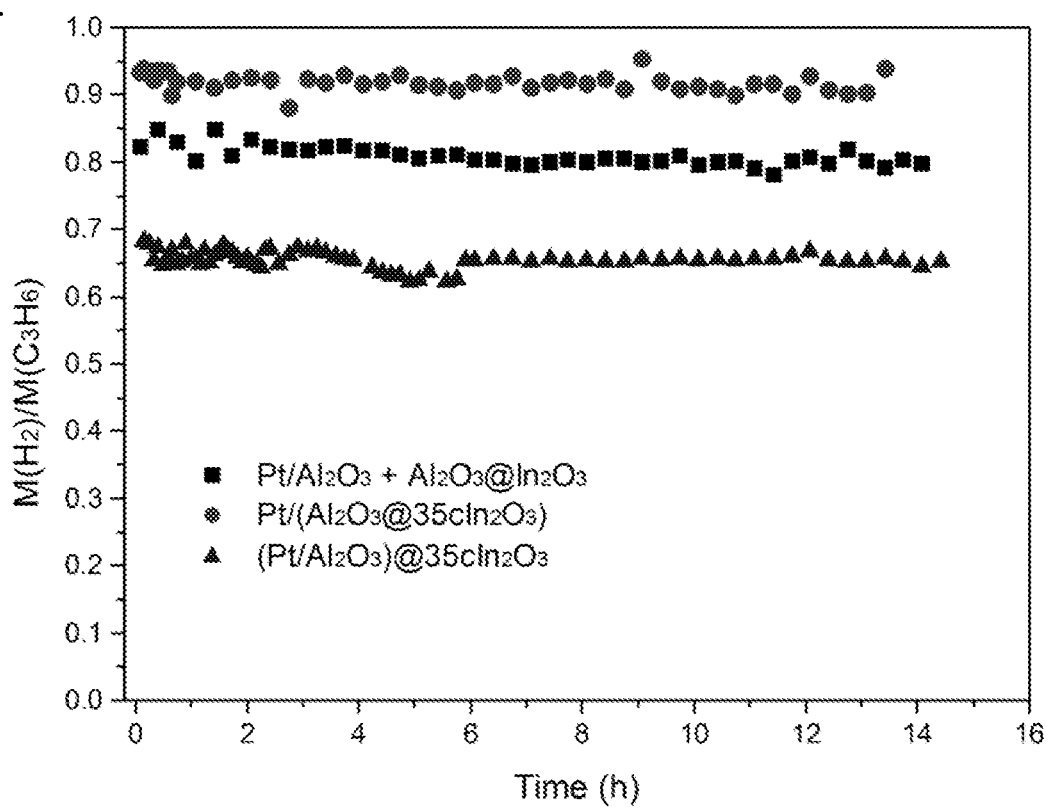
FIG. 4 shows the ratio of $H_2$ to propylene over different catalysts. T=450° C., $P_{C3H8}$:$P_{O2}$:$P_{N2}$=10:5:85 kPa. $WHSV^{-1}$=1.55 $kg_{C3H8}^{-1}$ $kg_{catalyst}$ h for the optimum catalyst and $Pt/(Al_2O_3@35cIn_2O_3)$, and 3.1 $kg_{C3H8}^{-1}$ $kg_{catalyst}$ for $Pt/Al_2O_3+Al_2O_3@In_2O_3$.

The second design, with Pt supported on 35 cycles of $In_2O_3$-ALD-coated $Al_2O_3$ (designated as Pt/($Al_2O_3$@35c$In_2O_3$)) initially produced a slightly higher propane conversion (27%), propylene selectivity (72%), and propylene yield (19%) than the physical mixture. However, it also deactivated rapidly over 1 hour TOS (FIG. 2E). As for the prior model, the Pt NPs were not protected from $O_2$ by the $In_2O_3$ coating, leading to poor propylene selectivity, even though the $In_2O_3$ component was able to carry out SHC and decrease the $H_2$/propylene ratio to 0.9 (FIG. 4). Similarly, in this model, the aggregation of the Pt NPs also contributed to the deactivation of the reaction. The particle size of Pt/($Al_2O_3$@35c$In_2O_3$) grew obviously from 2.0±0.7 nm to 6.0±7.3 nm after 14 hours TOS at 450° C. (FIGS. 2F-2H).

Figures 2I, 2J, 2K, 2L:
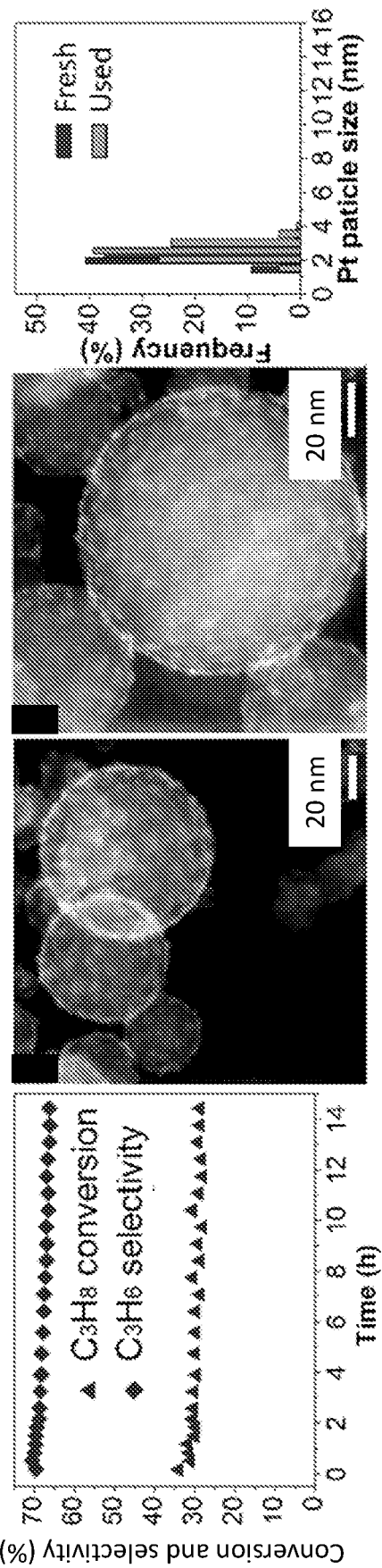
Figure 3:
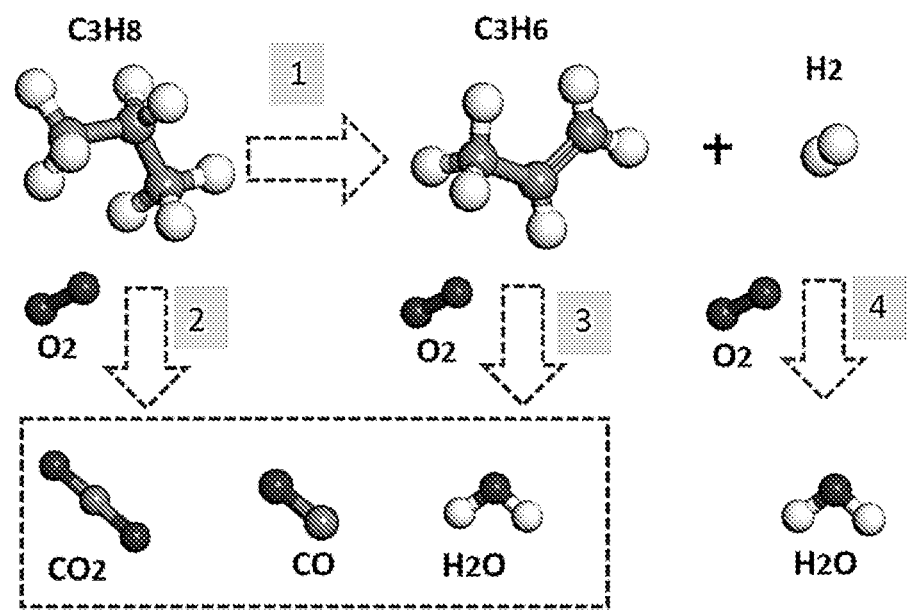
FIG. 3 shows a schematic for the tandem propane dehydrogenation (PDH)- selective hydrogen combustion (SHC) reaction network. In the case where PDH (Step 1) is the only reaction, the molar ratio of hydrogen (Hz) to propylene ($C_3H_6$) is 1.0, by stoichiometry. If excess propylene combustion occurs (Step 3), or if propane cracking occurs (not shown), the ratio will be higher than 1. If selective $H_2$ combustion occurs (Step 4), the ratio will be lower than 1.0.

The third design, having the layered structure (Pt/$Al_2O_3$)@35c$In_2O_3$, produced the highest propane conversion (32%), propylene selectivity (70%), and propylene yield (22%) of the three designs and, notably, maintained this high performance for 14 hours TOS without significant deactivation (FIG. 2I). Moreover, the H₂/propylene ratio produced by the layered design was the lowest at about 0.6 (FIG. 4), demonstrating the efficacy of the SHC component. In addition to improving selectivity, the $In_2O_3$ overcoat stabilized the Pt NPs, whose size (2.0±0.8 nm) was essentially unchanged after 14 hours of reaction at 450° C. (FIGS. 2J-2L). The results from the three designs demonstrate that high propylene selectivity, a low H₂/propylene ratio, and high stability were enabled by the layered design more than with any other nanostructured arrangement.

Figure 5A:
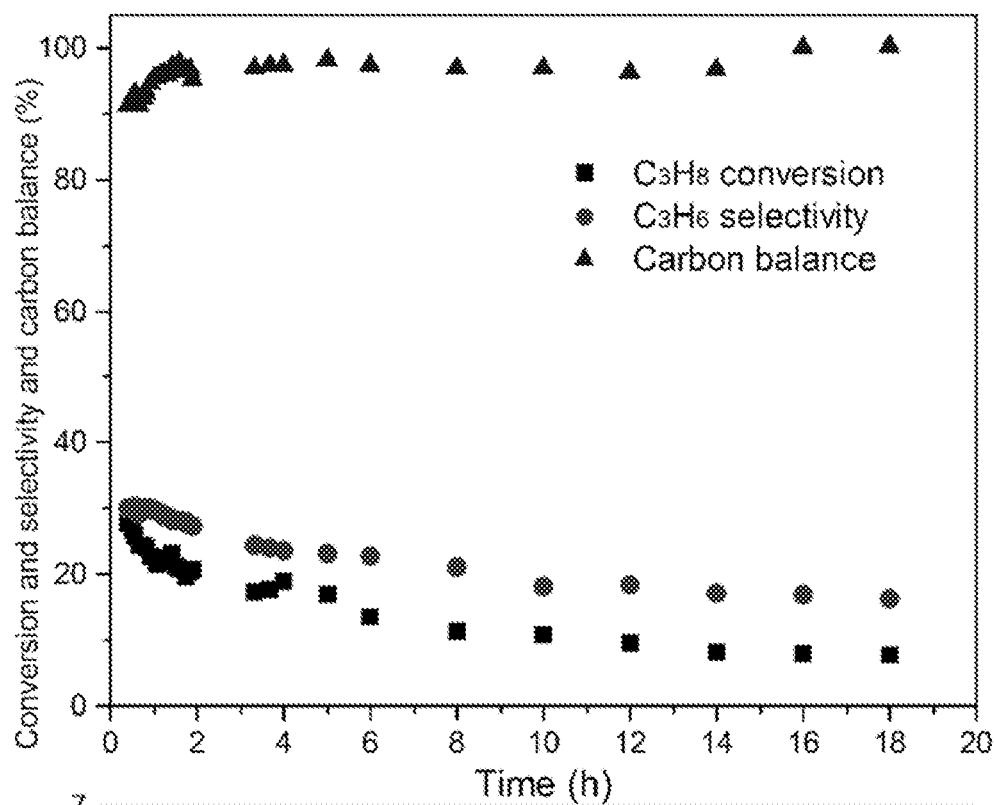
FIGS. 5A-5B show the catalytic performance of the tandem PDH-SHC reaction on uncoated Pt/Al$_2$O$_3$.
Figure 5B:
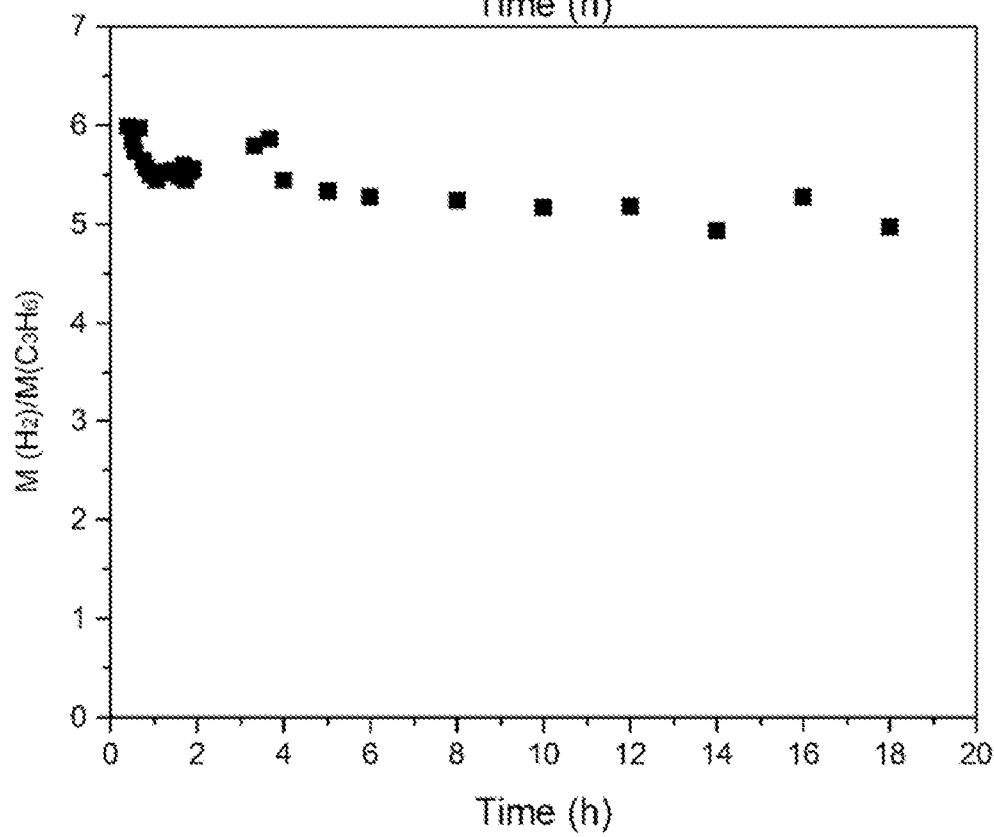

As a benchmark for comparison to the tandem catalyst designs, experiments were performed using just Pt/$Al_2O_3$ under reaction conditions of 450° C., $P_{C3H8}$:$P_{O2}$:$P_{N2}$=10:5:85 kPa, and $WHSV^{-1}$=3.1 $kg_{C3H8}^{-1}$=$kg_{catalyst}$ h. At the beginning of the experiment, propane conversion and propylene selectivity were 27% and 30%, respectively, for an overall propylene yield of 8%. After 14 hours of reaction, the conversion and selectivity had fallen to 8% and 17%, respectively, corresponding to a propylene yield of 1.4% (FIGS. 5A-5B). Over the same time period, the $H_2$/propylene ratio ranged from 6 to 5, above the expected stoichiometric ratio, coincident with a carbon balance below 95%, consistent with coke formation. Combustion was the primary reaction catalyzed by Pt/$Al_2O_3$ under oxidizing conditions.

Figure 6:
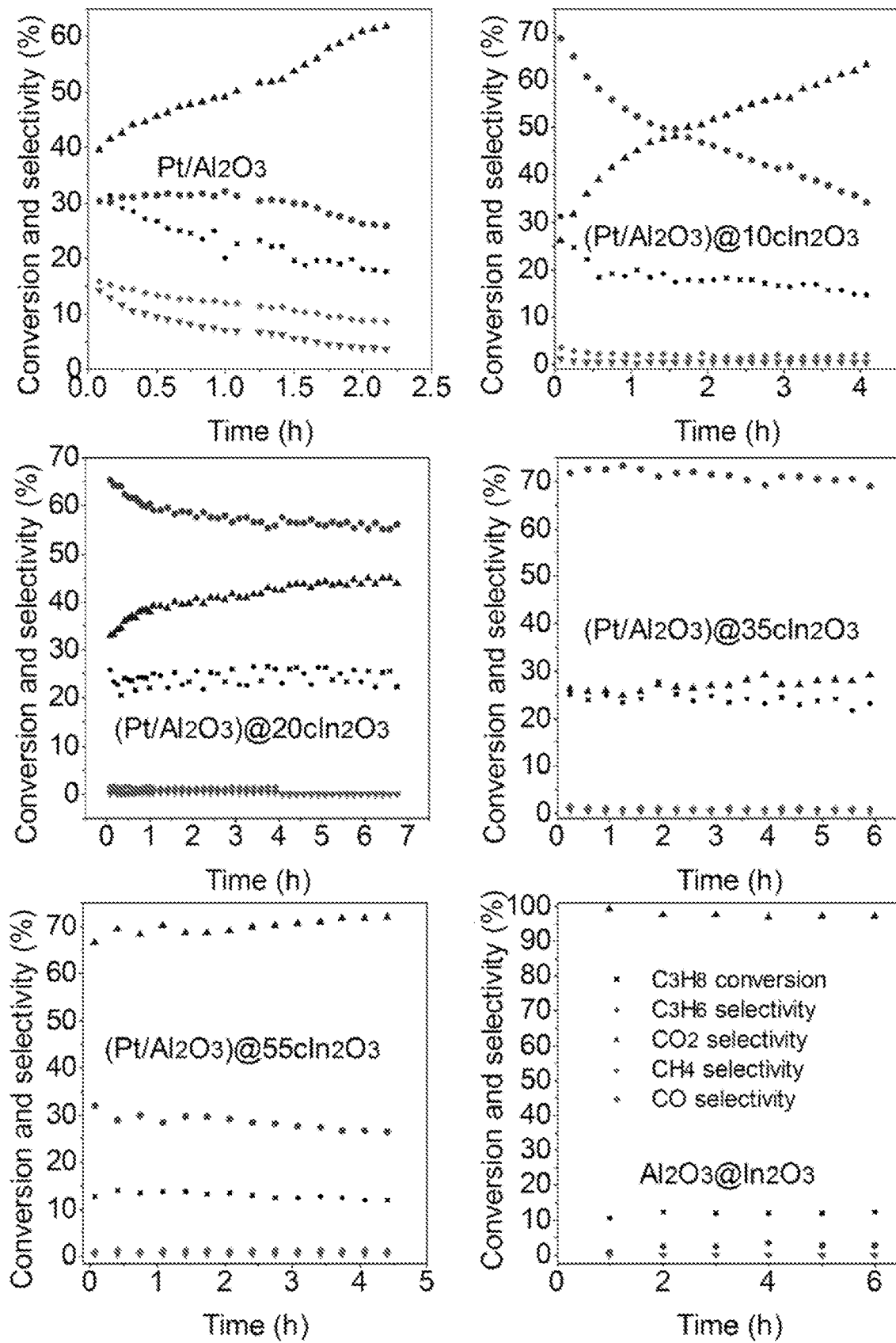
FIG. 6 shows propane conversion and product selectivity as a function of reaction time over various catalysts. T=450° C., propane: O$_2$=2:1, WHSV$^{-1}$=0.77 kg$_{C3H8}^{-1}$ kg$_{catalyst}$ h. The legend in the panel F applies to all panels.
Figure 7:
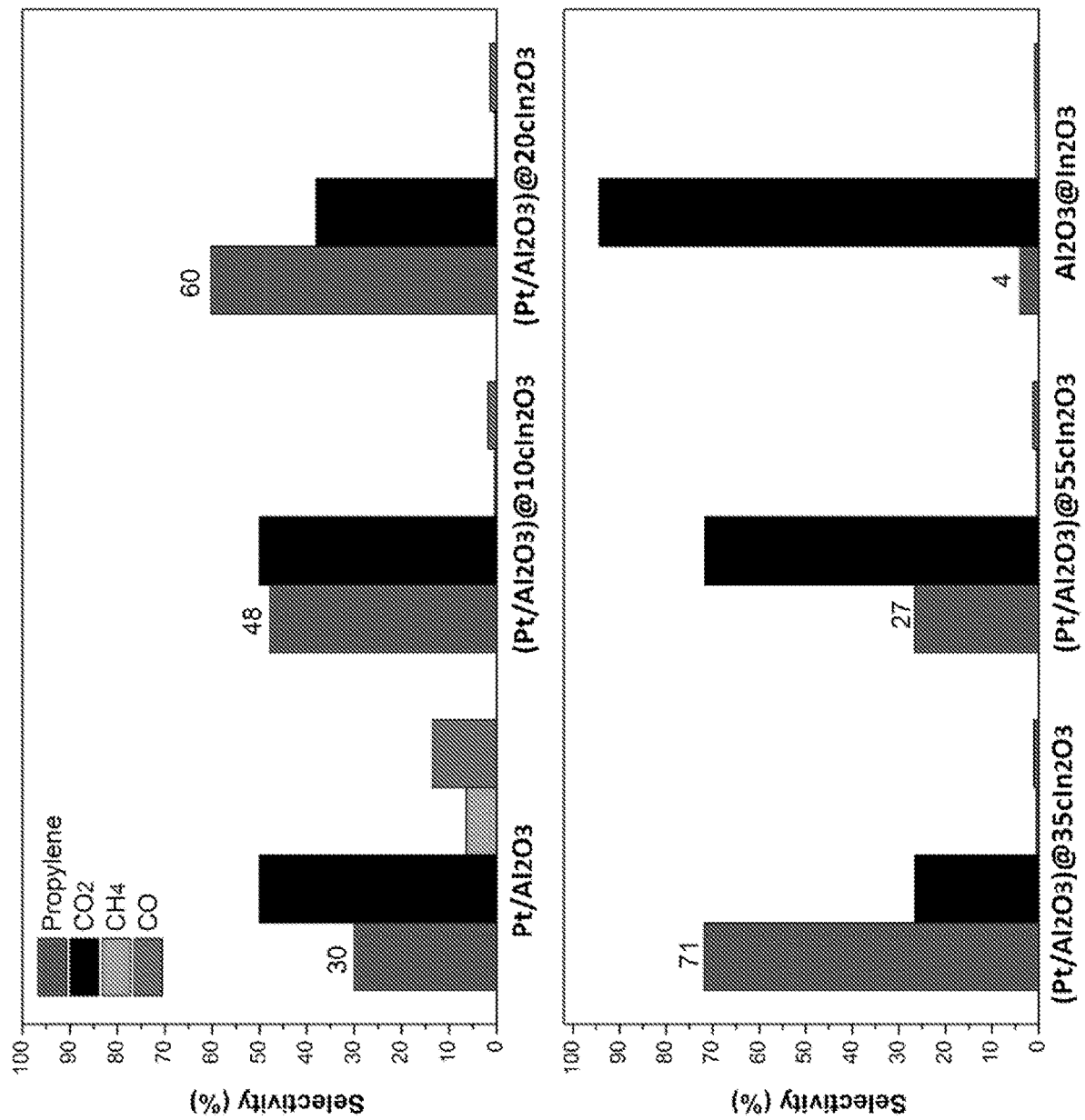
FIG. 7 shows product distributions over indium oxide-coated Pt/Al$_2$O$_3$ with different coating thicknesses (Pt/Al$_2$O$_3$@XcIn$_2$O$_3$, uncoated Pt/Al$_2$O$_3$, and indium oxide-coated alumina (Al$_2$O$_3$@In$_2$O$_3$). T=450° C., P$_{C3H8}$:P$_{O2}$:P$_{N2}$=10:5:85 kPa, WHSV$^{-1}$=0.77 kg$_{C3H8}^{-1}$ kg catalyst h. Product distributions were collected after 1 hour of reaction. The conversion for all the catalysts is ~20%, except for (Pt/Al$_2$O$_3$)@55cIn$_2$O$_3$ (14% conversion) and Al$_2$O$_3$@In$_2$O$_3$ (12% conversion).

The influence of $In_2O_3$ thickness was examined at $WHSV^{-1}$=0.77 $kg_{C3H8}^{-1}$ $kg_{catalyst}$ h by testing materials with 10, 20, 35, and 55 ALD cycles of $In_2O_3$. A catalyst with only 10 ALD cycles deactivated significantly over 4 hours, while materials with 10 or more ALD cycles exhibited stable performance. Both propane conversion and propylene selectivity increased monotonically with the number of $In_2O_3$ ALD cycles, up to maximum values at 35 cycles of $In_2O_3$ ALD coating (FIGS. 6 and 7). Beyond 35 cycles, conversion and selectivity fell to values which were more consistent with an $Al_2O_3$@$In_2O_3$ catalyst containing no Pt. Because of its high stability and selectivity, Pt/$Al_2O_3$ coated by 35 cycles of $In_2O_3$ ALD (designated as (Pt/$Al_2O_3$)@35c$In_2O_3$) was selected for further investigation, and it is henceforth referred to as the "optimum catalyst" unless otherwise specified.

Figure 8:
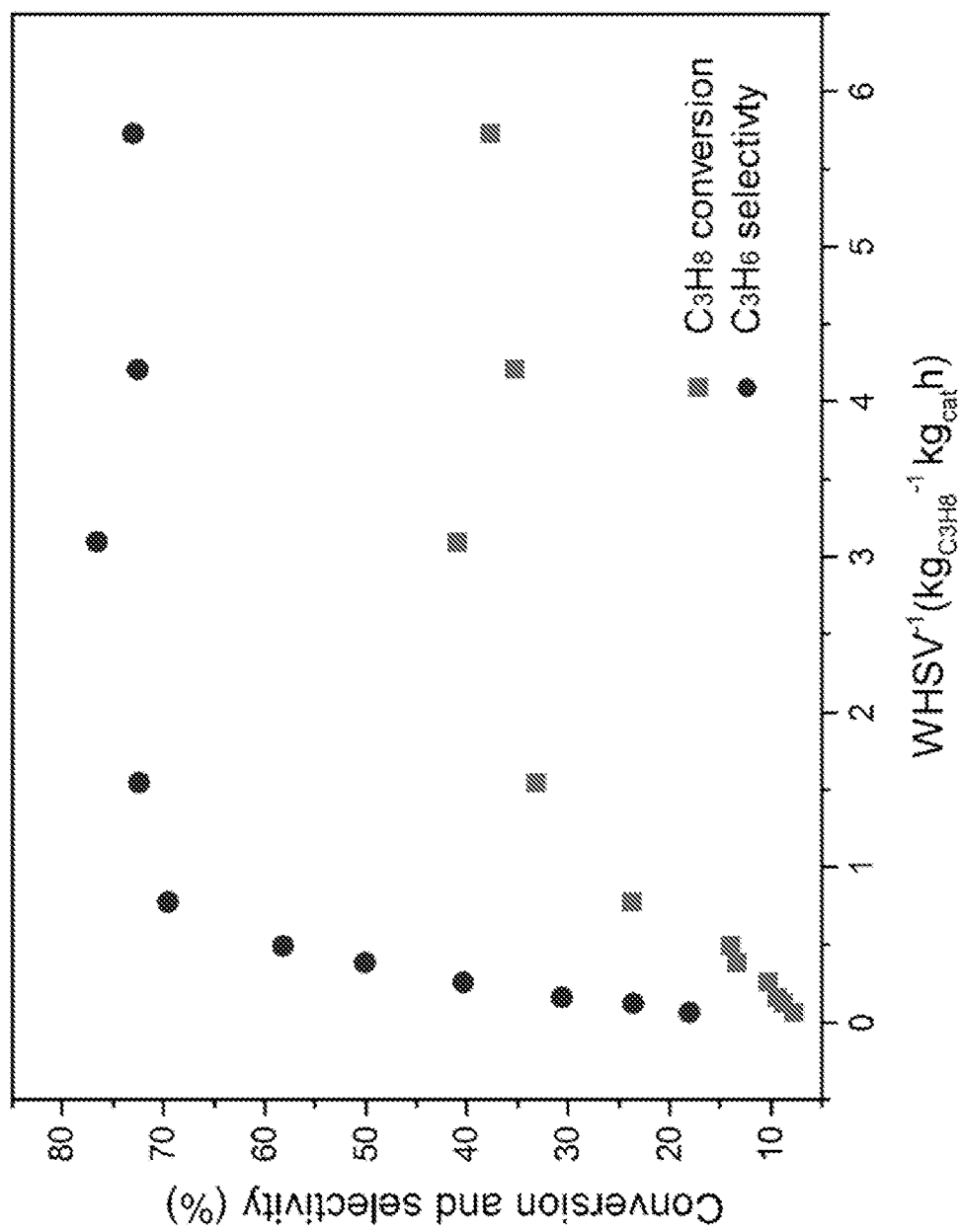
FIG. 8 shows propane conversion and propylene selectivity as a function of WHSV$^{-1}$ over (Pt/Al$_2$O$_3$)@35cIn$_2$O$_3$ (optimum catalyst). T=450° C., P$_{C3H8}$:P$_{O2}$:P$_{N2}$=10:5:85 kPa. For WHSV$^{-1}$ below 3.1 kg$_{C3H8}^{-1}$ kg$_{catalyst}$ h, flow rates were decreased from 200 to 8 sccm with the same amount of catalyst. For WHSV$^{-1}$=4.1 and 5.7 kg$_{C3H8}^{-1}$ kg$_{catalyst}$ h, catalyst masses were increased at a total flow rate of 8 sccm. Fresh catalysts were used for every data point.
Figure 9:
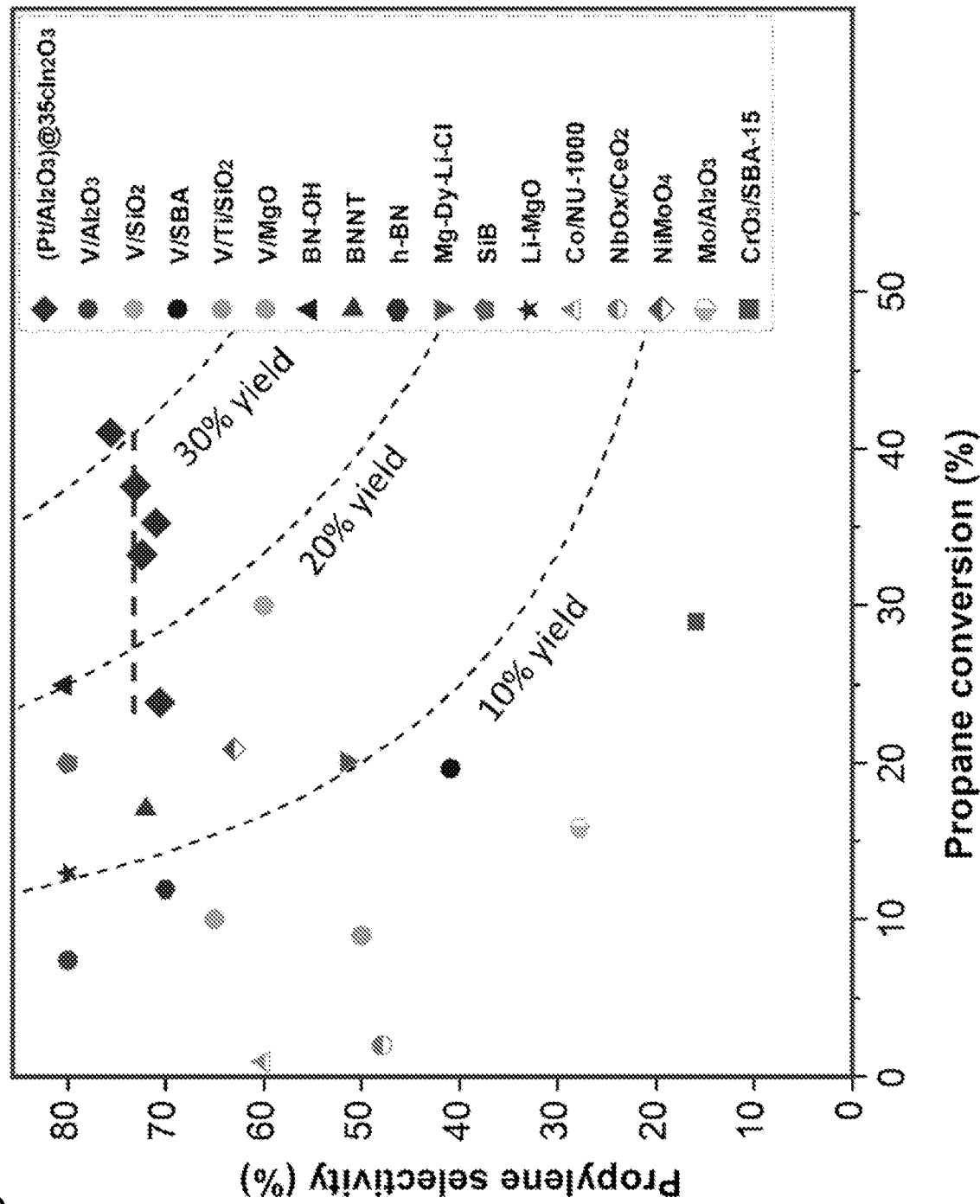
FIG. 9 compares the catalytic performance of established ODHP catalysts with (Pt/Al$_2$O$_3$)@35cIn$_2$O$_3$ (optimum catalyst). Propane conversion over the optimum catalyst was obtained by changing the inverse weight hour space velocity (WHSV$^{-1}$) from 0.77 to 5.72 kg$_{C3H8}^{-1}$ kg$_{catalyst}$ h at 450° C. with C$_3$H$_8$:O$_2$=2:1. Black dashed lines show 10%, 20% and 30% propylene yield.
Figure 10:
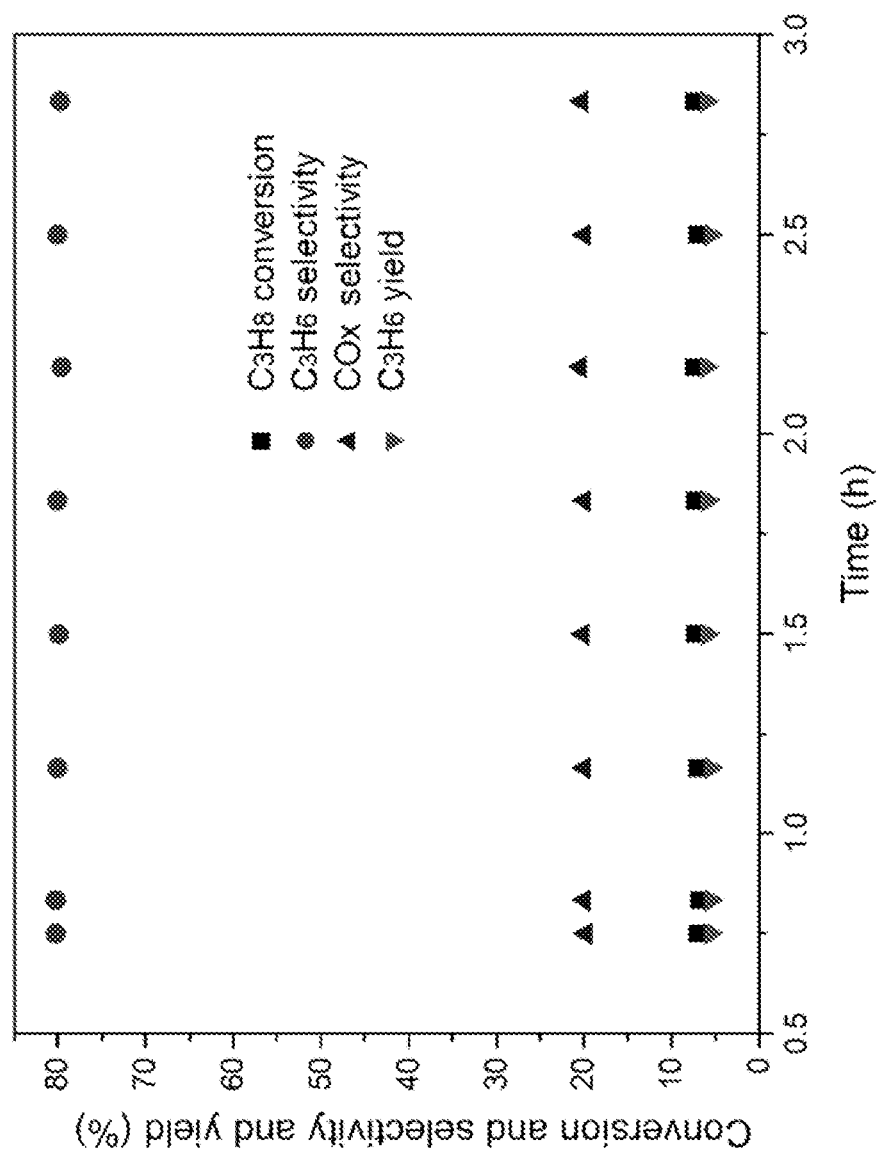
FIG. 10 shows catalytic performance of the ODHP reaction over VO$_x$/Al$_2$O$_3$ (1 wt. %) at 450° C. Propane conversion, propylene and CO$_x$ selectivity, and propylene yield as a function of reaction time on stream. P$_{C3H8}$:P$_{O2}$:P$_{N2}$=10:5:85 kPa, WHSV$^{-1}$=0.77 kg$_{C3H8}^{-1}$ kg$_{catalyst}$ h.

For the optimum catalyst, the contact time was varied and the best combined performance of 76% selectivity at 40% conversion was achieved at $WHSV^{-1}$=3.1 $kg_{C3H8}^{-1}$ $kg_{catalyst}$ h (FIG. 8). The propylene yield (30%) substantially exceeded the highest per-pass yields reported for state-of-the-art ODHP catalysts operating under comparable reaction conditions (FIG. 9). Notably, a stable 37% yield was achieved at 500° C. These results were benchmarked against a $VO_x$/$Al_2O_3$ catalyst synthesized in-house, and it showed a high propylene yield (FIG. 10).

Figure 11A:
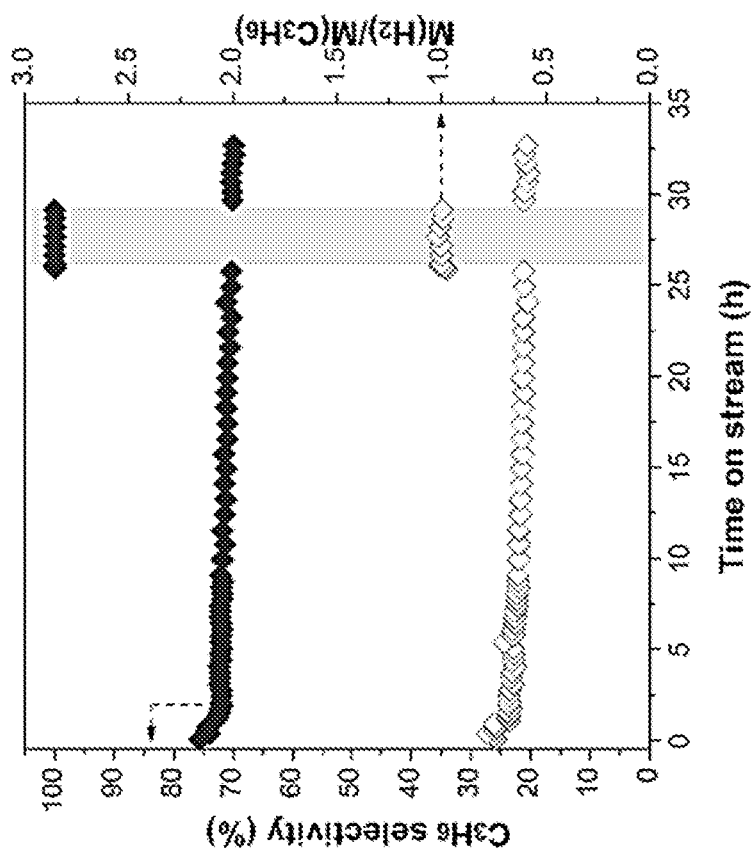
FIGS. 11A-11B show catalytic performance of the tandem PDH-SHC reaction on (Pt/Al$_2$O$_3$)@35cIn$_2$O$_3$ (optimum catalyst).
Figure 11B:
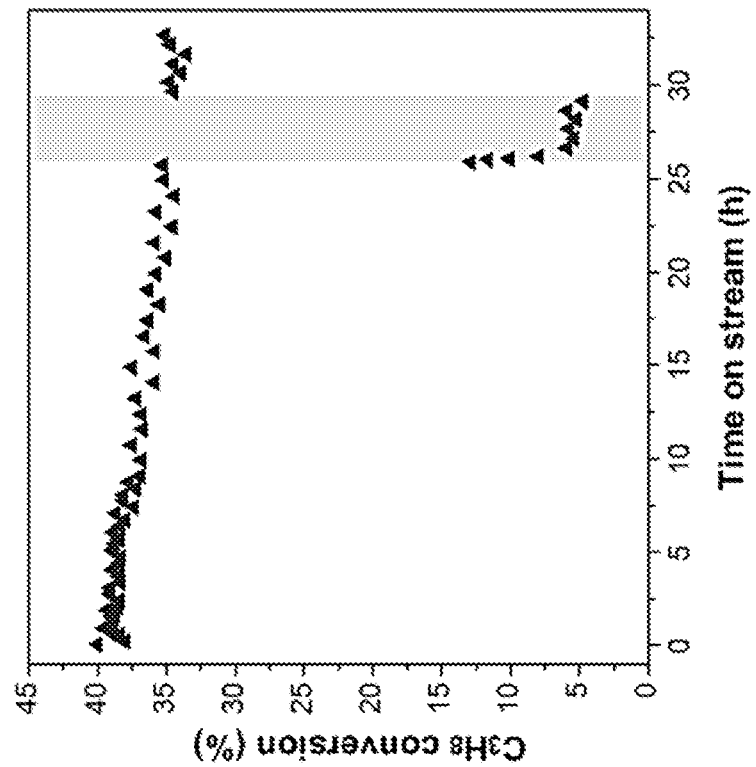
Figure 12:
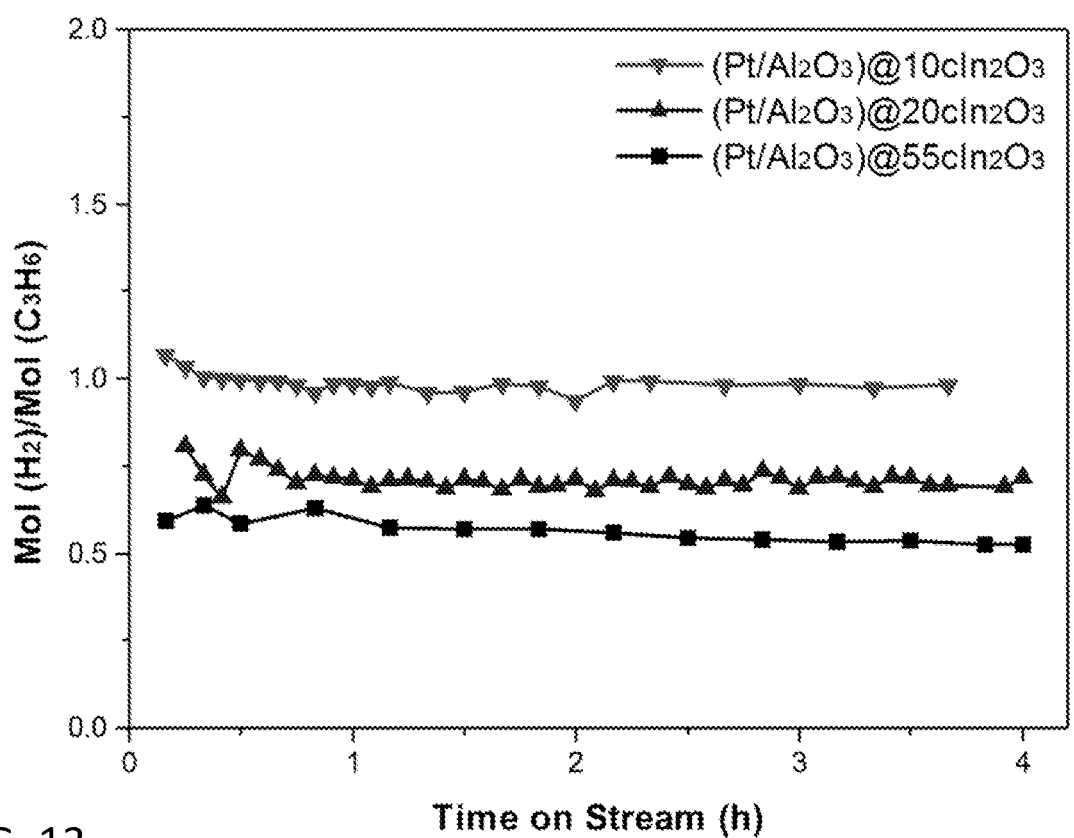
FIG. 12 shows the ratio of H$_2$ to propylene over 10, 20 and 55 cycles of indium oxide-coated Pt/Al$_2$O$_3$ with different coating thicknesses, (Pt/Al$_2$O$_3$)@XcIn$_2$O$_3$. T=450° C., propane: O$_2$=2:1, WHSV$^{-1}$=0.77 kg$_{C3H8}^{-1}$ kg$_{catalyst}$ h.
Figure 13:
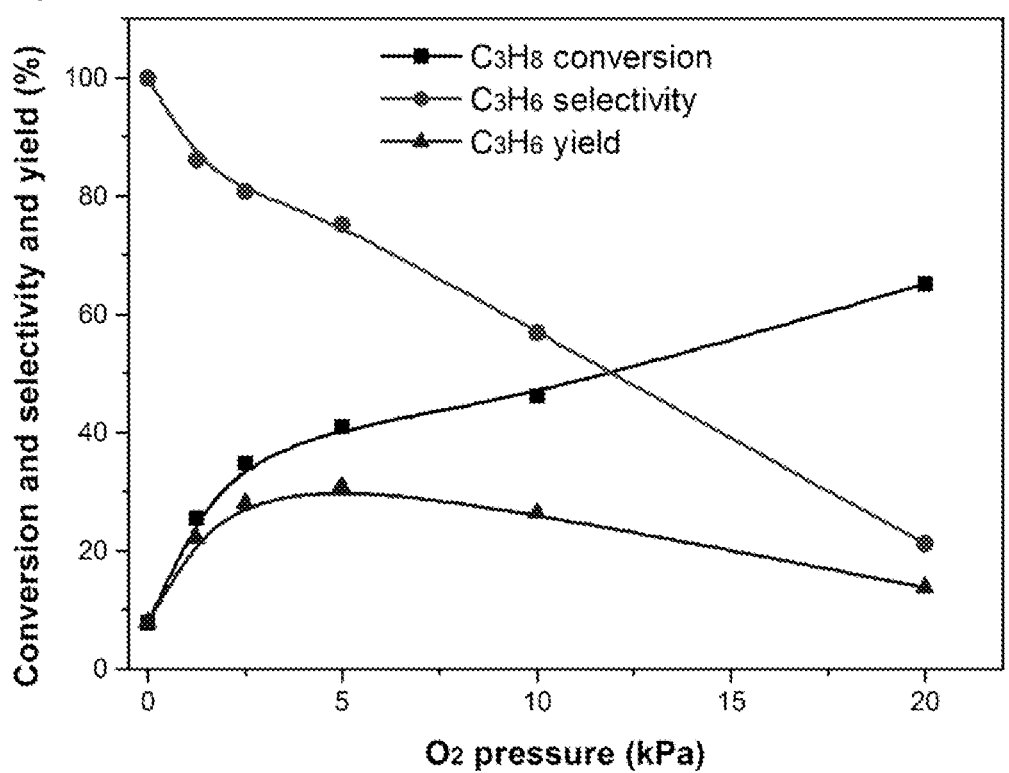
FIG. 13 shows propane conversion, propylene selectivity, and yield as a function of O$_2$ pressure, over the optimum catalyst, (Pt/Al$_2$O$_3$)@35cIn$_2$O$_3$. T=450° C., P$_{C3H8}$=10 kPa, balance N$_2$ at a nominal total pressure of 100 kPa. WHSV$^{-1}$=3.1 kg$_{C3H8}^{-1}$ kg$_{catalyst}$ h. The highest propylene yield was achieved at an O$_2$:propylene ratio of 1:2, but the yield was relatively flat at a range of O$_2$ partial pressures. Overall, increasing O$_2$ increases combustion, which increases propane conversion but lowers propylene selectivity.
Figure 14:
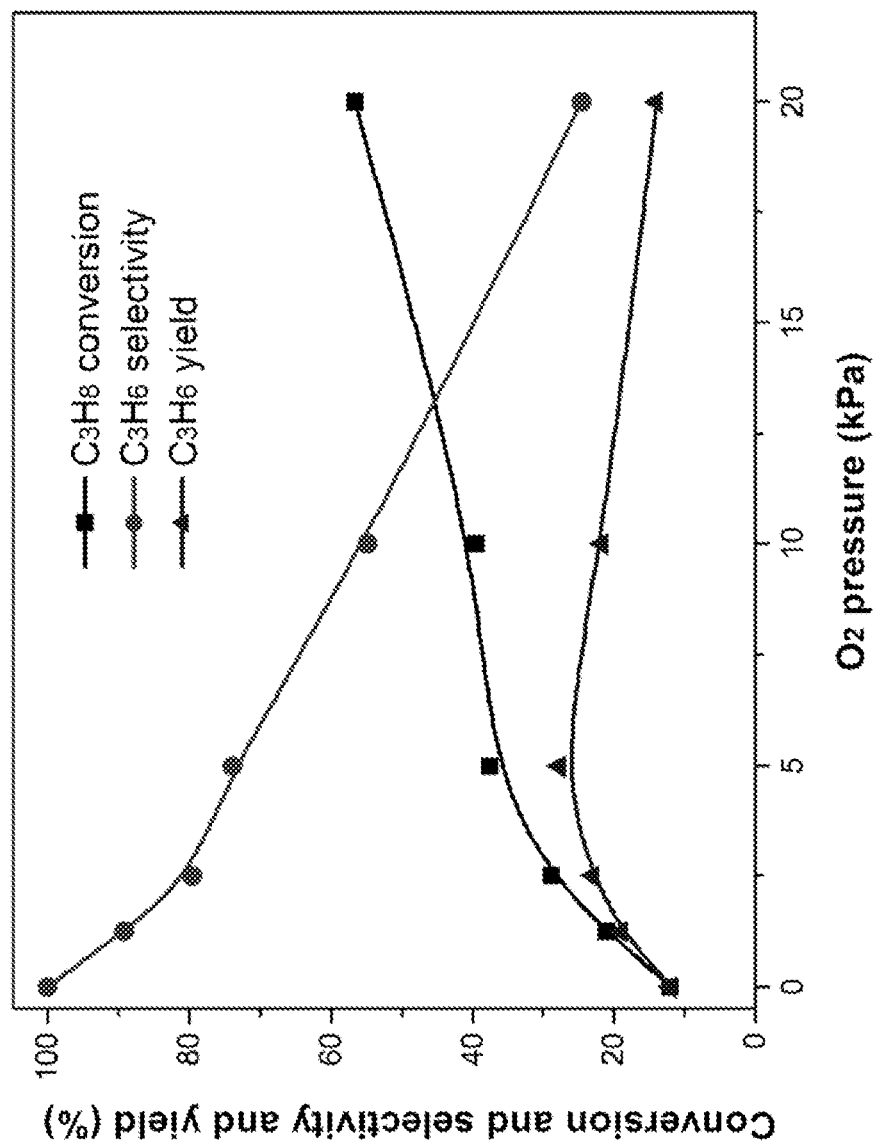
FIG. 14 shows propane conversion, propylene selectivity, and yield as a function of O$_2$ pressure, over the optimum catalyst, (Pt/Al$_2$O$_3$)@35cIn$_2$O$_3$. T=450° C., P$_{C3H8}$=10 kPa, balance N$_2$ at a nominal total pressure of 100 kPa. WHSV$^{-1}$=5.7 kg$_{C3H8}^{-1}$ kg$_{catalyst}$ h. The highest propylene yield was achieved at an O$_2$:propylene ratio of 1:2, but the yield was relatively flat at a range of O$_2$ partial pressures. Overall, increasing O$_2$ increases combustion, which increases propane conversion but lowers propylene selectivity.

The optimum catalyst was highly active, stable, and selective. Over 32 hours, propane conversion decreased only slightly from 40% to ~35% (FIG. 11A). These figures exceed the equilibrium conversion ~24% for non-oxidative PDH at these reaction conditions, and was much higher than the conversion achievable by the tandem catalyst without an $O_2$ feed (6%). (K. J. Caspary et al., *Handbook of Heterogeneous Catalysis: Online*, 3206-3229 (2008); D. E. Resasco, Dehydrogenation-heterogeneous. *Encyclopedia of Catalysis*, (2002); F. E. Frey et al., *Ind. Eng. Chem. Res.* 25, 54-59 (1933).) Following the cut in $O_2$, conversion and selectivity immediately recovered upon reintroducing $O_2$ (FIG. 11A), further demonstrating the stability of the catalyst. During the 32 hours TOS, the propylene selectivity also remained >70% without any obvious decrease (FIG. 11B). Outlet H₂/propylene ratios provide evidence for the proposed tandem catalysis (FIG. 11B and FIG. 12). The theoretical H₂/propylene ratio from PDH (1.0) was achieved for the tandem catalyst in the absence of added $O_2$ (FIG. 11B), while in the presence of $O_2$, the optimum catalyst gave a $H_2$/propylene ratio of 0.6, indicative of selective $H_2$ combustion, as desired. The crucial role of $O_2$ was further studied by varying the $O_2$ partial pressure. At a propane pressure of 10 kPa, selectivity over the optimum catalyst decreased and conversion increased as $O_2$ pressure increased from 0 to 20 kPa (FIGS. 13 and 14). The highest yield occurred when the pressure ratio of propane to $O_2$ was 2. Taken together, the low ratio of $H_2$ to propylene and the enhanced propylene yield indicate that the hydrogen combustion catalyzed by the $In_2O_3$ strongly pulled the PDH equilibrium forward by the consumption of $H_2$.

Figure 15A:
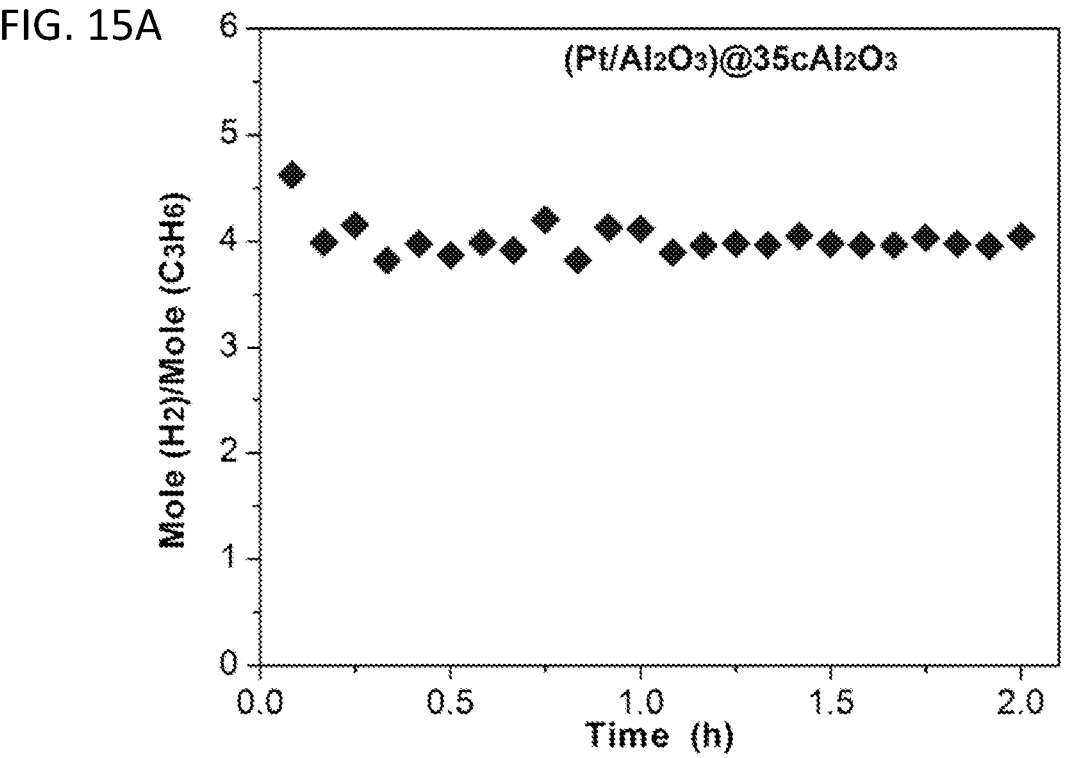
FIGS. 15A-15B show catalytic performance of (Pt/Al$_2$O$_3$)@35 cAl$_2$O$_3$ for PDH-SHC.
Figure 15B:
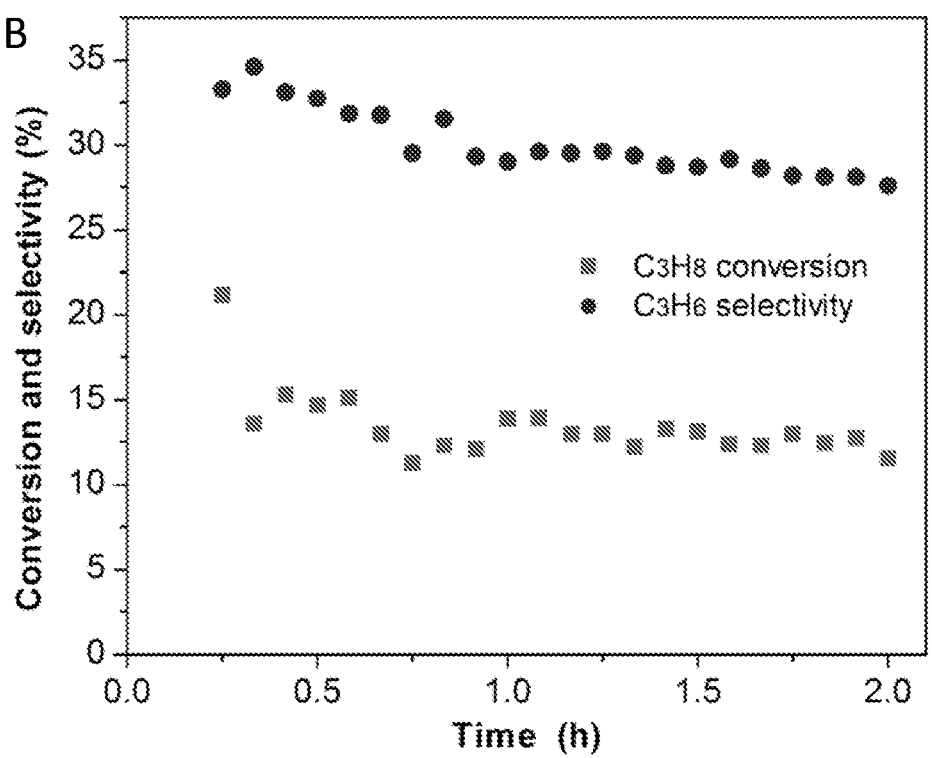
Figure 16A:
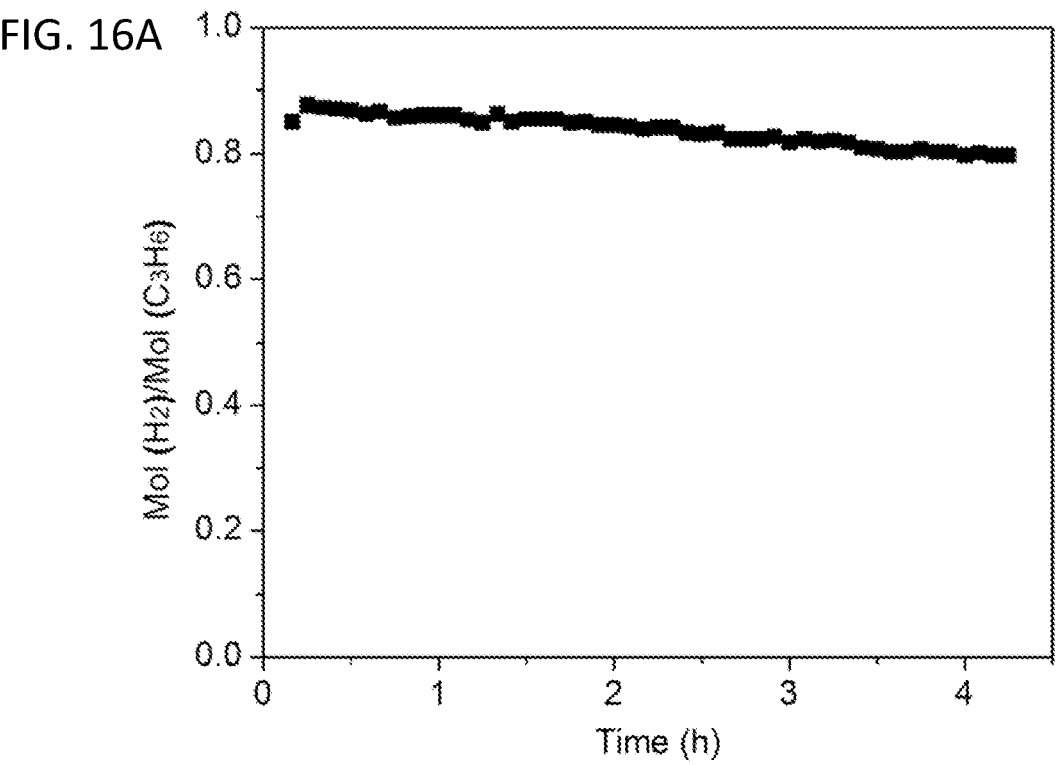
FIGS. 16A-16B show catalytic performance of a physical mixture of (Pt/Al$_2$O$_3$)@35 cAl$_2$O$_3$ and Al$_2$O$_3$@In$_2$O$_3$ materials for PDH-SHC.
Figure 16B:
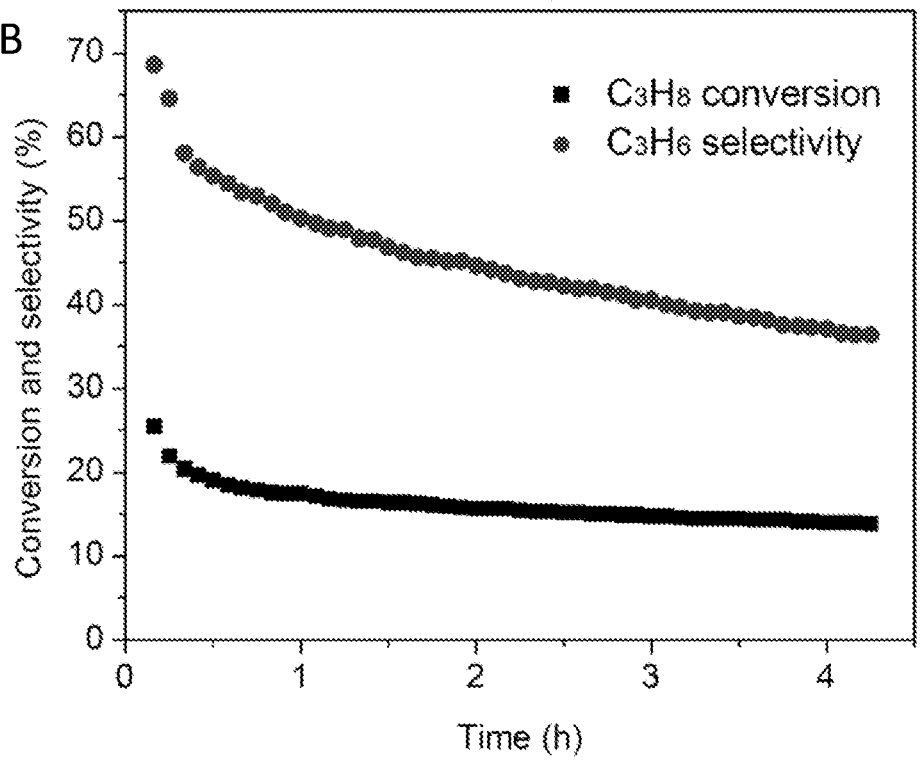

Finally, a fourth tandem catalyst design composed of a Pt/$Al_2O_3$ powder stabilized by overcoating with alumina ALD, (Pt/$Al_2O_3$)@35 c$Al_2O_3$, physically mixed with $Al_2O_3$@$In_2O_3$ was tested. (Pt/$Al_2O_3$)@35 c$Al_2O_3$, alone, gave a propylene yield of ~5% and a H₂/propylene ratio of 4, similar to uncoated Pt/$Al_2O_3$ (FIG. 15A) but exhibited higher stability (FIG. 15B). A physical mixture of (Pt/$Al_2O_3$)@35 c$Al_2O_3$ and $Al_2O_3$@$In_2O_3$ initially increased the propylene selectivity and showed a low H₂/propylene ratio of 0.8 (FIG. 16A), consistent with SHC by the $Al_2O_3$@$In_2O_3$ particles. However, the catalyst still deactivated, and the propylene selectivity rapidly fell to 35% in 4 hours TOS, corresponding to a <7% propylene yield (FIG. 16B). This last design emphasizes the importance of having an overcoat that participates in tandem catalysis, rather than one that just stabilizes the Pt nanoparticles.

The catalysts were characterized by electron microscopy; IR, X-ray photoelectron, and X-ray absorption spectroscopies; and physical measurements. STEM showed that $In_2O_3$ uniformly coated the Pt/$Al_2O_3$ (FIG. 17A), and that the Pt particle size distribution was unchanged by the overcoating process. Energy dispersive X-ray spectroscopy elemental analysis (EDS) mapping of indium Lα confirmed a conformal coating of indium in the oxide form on Pt/$Al_2O_3$ (FIG. 17A). The thickness of the $In_2O_3$ was ~2.0 nm (FIG. 17B) after 35 cycles of $In_2O_3$ ALD. The porosity of the $In_2O_3$ coated catalysts were determined by CO adsorption diffuse reflectance infrared spectroscopy (CO DRIFTS) and $N_2$ physisorption measurements. As shown in FIG. 17C, CO adsorbed on the uncoated Pt/$Al_2O_3$ catalyst exhibited two main peaks at 2087 and 2066 $cm^{-1}$, which were assigned to linear CO adsorption on Pt NPs with different particle sizes. However, there were no obvious features from a freshly prepared optimum catalyst, indicating the Pt NP surfaces were totally covered by $In_2O_3$ overcoats immediately after $In_2O_3$ ALD. When the sample was gradually heated to the reaction temperature (450° C.) under $N_2$, chemisorbed CO was detected beginning at 200° C., and was pronounced by 450° C. Samples with different numbers of indium oxide layers gave similar trends.

Figure 18:
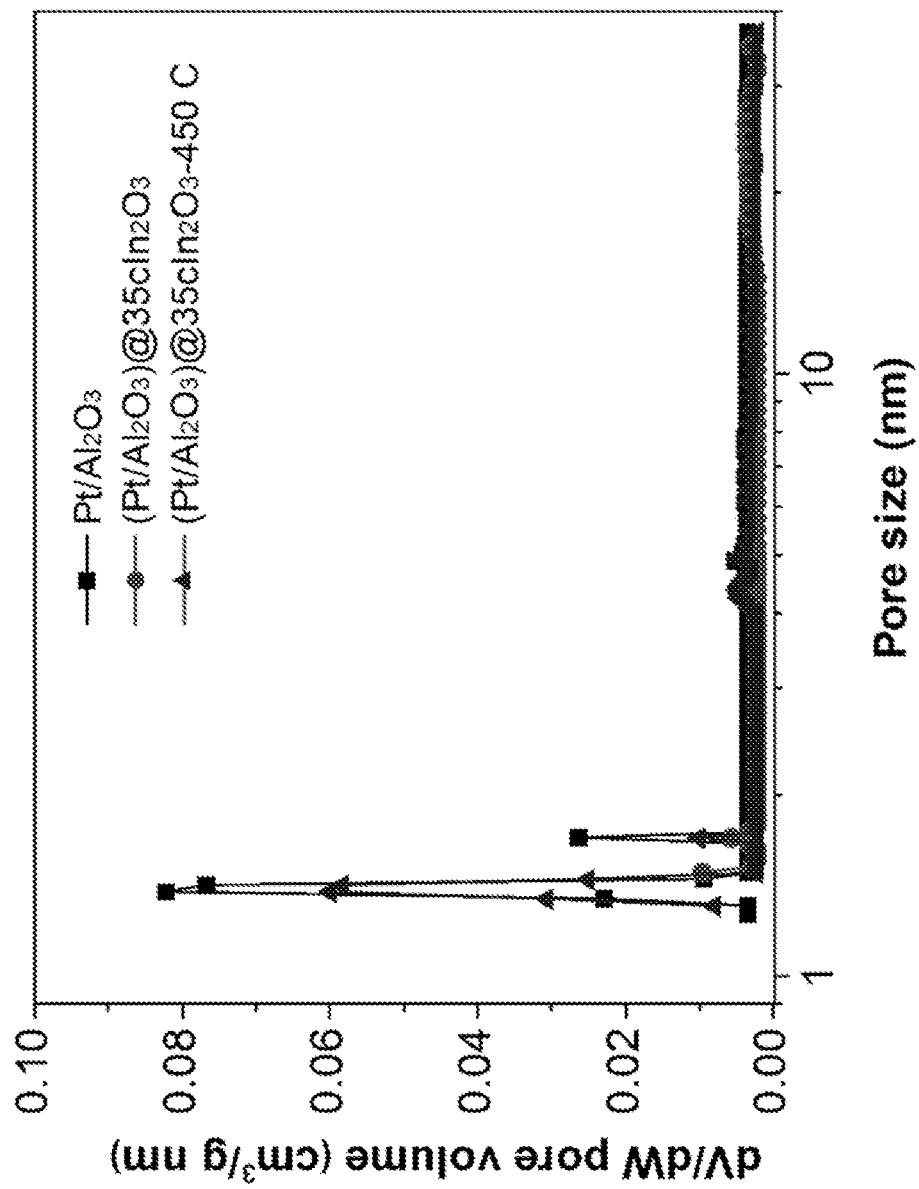
FIG. 18 shows density functional theory (DFT) pore size distribution on Pt/Al$_2$O$_3$, freshly-synthesized (Pt/Al$_2$O$_3$)@35cIn$_2$O$_3$ (the optimum catalyst), and the same catalyst after pretreatment at 450° C. in nitrogen for 1 hour.
Figure 19:
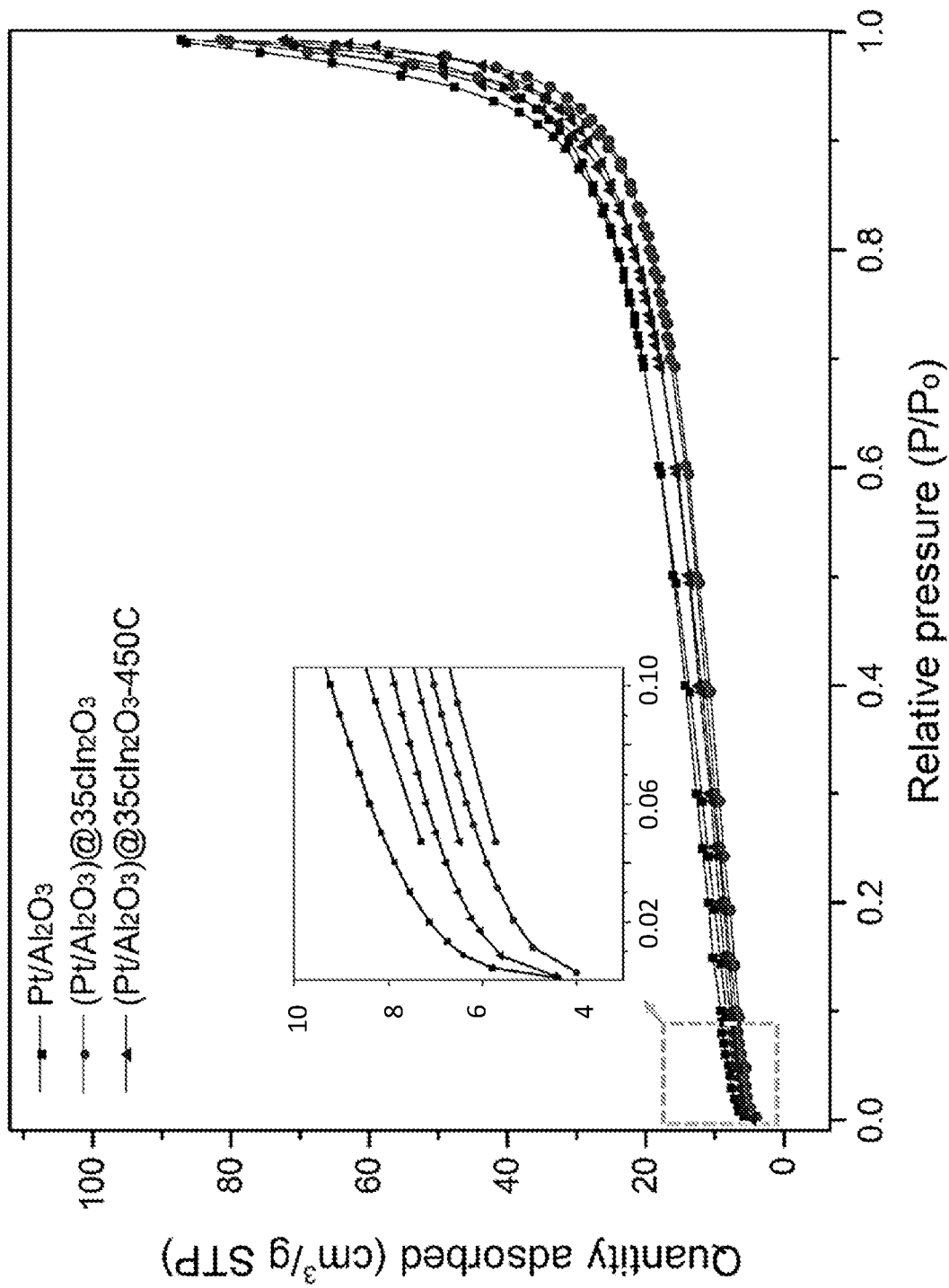
FIG. 19 shows nitrogen adsorption-desorption isotherms on uncoated Pt/Al$_2$O$_3$, freshly-synthesized (Pt/Al$_2$O$_3$)@35cIn$_2$O$_3$ (the optimum catalyst), and the same catalyst after pretreating at 450° C. in nitrogen for 1 hour. Isotherms normalized by the weight of the starting catalyst. The inset shows the isotherms at pressure <0.1 P/P$_0$.

According to the $N_2$ physisorption data (FIGS. 18 and 19), the original, uncoated Pt/$Al_2O_3$ showed some microporosity, with an average pore size of 1.4 nm. The micropores disappeared for the freshly-synthesized optimum catalyst, indicating the surface was totally covered by the $In_2O_3$ coating. After pretreatment at 450° C., the microporosity returned. The formed porosity made the coated Pt nanoparticles accessible to reagents, consistent with the CO DRIFTS results. CO pulse chemisorption was performed on the optimum catalyst to quantify the extent of exposed Pt on Pt NPs. Pt/$Al_2O_3$ showed 2.10 mmol CO $g_{Pt}^{-1}$ (FIG. 17D), equivalent to a Pt dispersion of 41% and in good agreement with the size of the Pt nanoparticles observed in STEM images. The freshly optimum catalyst chemisorbed only 0.015 mmol CO $g_{Pt}^{-1}$, but after a 450° C. heat treatment, the value increased to 1.14 mmol CO $g_{Pt}^{-1}$, demonstrating that approximately half of the surface Pt atoms had been rendered accessible again.

Compared with Pt/$Al_2O_3$, the X-ray photoelectron spectra (XPS) showed identical Pt $4d_{5/2}$ binding energy on the used tandem catalyst, indicating no Pt-In alloy formation after the tandem PDH-SHC reaction at 450° C. X-ray absorption spectra further confirmed the same electronic states between the used optimum catalyst and Pt/$Al_2O_3$. Likewise, there was no obvious change of indium electronic state between the fresh and used optimum catalyst, and the peak ($3d_{5/2}$) location at 445.1 eV was indicative of $In_2O_3$ rather than more the metallic character of Pt—In alloys. The absence of alloy was not surprising because the Pt- and Pd—In alloys typically form above 600° C. Therefore, after 35 cycles of $In_2O_3$ ALD coating and heating at 450° C. in $N_2$, an $In_2O_3$ coating was synthesized with 2.0 nm thickness and having micropores that enabled controlled access to the underlying Pt NP surface.

Among the various tandem catalyst designs, Hz/propylene ratios decreased as the connection between Pt NPs and $In_2O_3$ became more intimate. $H_2$-temperature-programmed reduction (TPR) measurements showed that this was due to enhanced $H_2$ combustion activity by contact between Pt and $In_2O_3$. $Al_2O_3$@$In_2O_3$ and the physical mixture Pt/$Al_2O_3$+$Al_2O_3$@$In_2O_3$ exhibited $H_2$-TPR peaks and $H_2O$ production from 250 to 350° C. In contrast, materials with intimate Pt-$In_2O_3$ contact, namely the layered catalyst (optimum catalyst) and Pt/($Al_2O_3$@35c$In_2O_3$), exhibited reduction at lower temperatures from 110 to 280° C. Therefore, materials having an extensive Pt-$In_2O_3$ interface were more effective for the tandem PDH-SHC by providing a pathway for reaction between chemisorbed hydrogen and $In_2O_3$.

Materials and Methods

Trimethyl(methylcyclopentadienyl)platinum(IV) (MeCpPtMe$_3$, 99.9%) and cyclopentadienyl indium (InCp, 99.99%) were purchased from Strem Chemicals. Trimethylaluminum (TMA, 97%) was purchased from Sigma-Aldrich. $Al_2O_3$ nanodur (BET surface area 32-40 $m^2/g$) was purchased from Alfa Aesar. Ultrahigh purity $N_2$ (99.999%), $O_2$ (99.994%), He (99.999%), propane (99.0%) and dry synthetic air were all provided by Airgas. All chemicals were used as received without further purification.

Synthesis of Pt/$Al_2O_3$

One cycle of Pt ALD was performed to prepare the Pt/$Al_2O_3$ material. The Pt deposition was performed in a commercial, viscous flow reactor (GEM-STAR ALD, Arradiance). Nitrogen (99.999%) was used as the carrier gas. The precursor for platinum ALD was trimethyl(methylcyclopentadienyl) platinum(IV) (MeCpPtMe$_3$, Strem Chemical, 99%), and ozone was used as the oxidant to remove the ligand. To get sufficient vapor pressure, the precursor bubbler was heated to 65° C. The deposition chamber and chamber door were held at 225° C. To avoid condensation of the precursor, the manifold temperature was held at 115° C. The timing sequence was 200, 120, 200 and 120 seconds for MeCpPtMe$_3$ exposure, nitrogen purge, ozone exposure and nitrogen purge respectively. The Pt loading was 1.3 wt. %, confirmed by inductively coupled plasma optical emission spectroscopy (ICP-OES).

Synthesis of Indium Oxide Coated Pt/$Al_2O_3$ and Indium Oxide Coated $Al_2O_3$

Cyclopentadienyl indium (InCp, Strem Chemical, 99.99%) was used as the indium precursor, and ozone was used to remove the ligand. To get sufficient vapor pressure, the precursor bubbler was heated to 50° C. The deposition temperature was 150° C. To avoid condensation of the indium precursor on the inner walls, the manifold temperature was held at 115° C. The dose timings for one cycle were 500, 200, 500 and 200s corresponding to InCp exposure, nitrogen purge, ozone exposure and nitrogen purge, respectively. Different cycles of indium ALD were carried out to obtain a series of indium oxide coated Pt/$Al_2O_3$ materials (designated as (Pt/$Al_2O_3$)@Xc$In_2O_3$). As a control experiment, 35 cycles of indium ALD was also performed on the $Al_2O_3$ support using the same ALD conditions (designated as $Al_2O_3$@$In_2O_3$).

Synthesis of Pt/($Al_2O_3$@35c$In_2O$)

One cycle of Pt ALD was performed on the $Al_2O_3$@$In_2O_3$ material. The timing sequence was 200, 120, 200 and 120 seconds for MeCpPtMe$_3$ exposure, nitrogen purge, ozone exposure and nitrogen purge, respectively. The Pt loading was 1.5 wt. %, confirmed by inductively coupled plasma optical emission spectroscopy (ICP-OES).

Synthesis of Alumina Coated Pt/$Al_2O_3$

Trimethylaluminium (TMA, Strem Chemical, 99.99%) vapor at room temperature was employed as the aluminum precursor, and ultrapure water (Milipore) was used to remove the ligands. The deposition temperature was 200° C. The dose timing for one cycle was 20, 200, 20 and 200s corresponding to TMA exposure, nitrogen purge, $H_2O$ exposure and nitrogen purge, respectively. 35 cycles of TMA ALD were carried out to obtain the alumina coated Pt/$Al_2O_3$ (designated as (Pt/$Al_2O_3$)@35 c$Al_2O_3$).

Tandem PDH-SHC Reaction

The reaction was performed in a quartz tube reactor at 1 atmosphere pressure. Typically, 270 mg Pt/$Al_2O_3$@35c$In_2O_3$ and 500 mg of quartz sand were blended together, and loaded into the reactor. The reactor was heated to 450° C. at a rate of 10° C./min under nitrogen atmosphere, then the feed gas was switched to the reaction mixture. The total flow rate of feed gas was 8 sccm, comprised of 0.8 sccm propane (Airgas, 99%), 2 sccm dry synthetic air (Airgas) and 5.2 sccm nitrogen (Airgas, 99.999%). Various conversions were obtained by changing the weight-hour-space-velocity (WHSV) with different flow rates at 450° C. Each gas was controlled by an individual mass flow controller (MKS instruments). All gas lines after the reactor were heated to 100° C. by heating tapes, and the products were analyzed online via an Agilent 3000A micro-GC using a thermal conductivity detector (TCD). The GC was equipped with three columns: MS-5A for analysis of $H_2$, $O_2$, $N_2$, $CH_4$ and CO; Plot U for analysis of $CO_2$, $C_2H_4$ and $C_2H_6$; and alumina for $C_2$-$C_5$ alkanes and alkenes. The GC was calibrated using standard gases. $CH_4$ was detected only for the bare $Pt/Al_2O_3$ catalyst. Neither $C_2H_4$ nor $C_2H_6$ were detected over any catalyst.

The conversion, propylene selectivity, propylene yield, overall carbon balance, and inverse weight-hour-space-velocity (WHSV$^{-1}$) were calculated by the equations below:

$$\text{Conversion} = \frac{y_{C_3H_8,0} - y_{C_3H_8}}{y_{C_3H_8,0}} * 100$$

$$C_3H_6 \text{ Selectivity} = \frac{3y_{C_3H_6}}{3y_{C_3H_6} + y_{CH_4} + y_{CO} + y_{CO_2}} * 100\%$$

$$CO_2 \text{ Selectivity} = \frac{y_{CO_2}}{3y_{C_3H_6} + y_{CH_4} + y_{CO} + y_{CO_2}} * 100\%$$

$$CO \text{ Selectivity} = \frac{y_{CO}}{3y_{C_3H_6} + y_{CH_4} + y_{CO} + y_{CO_2}} * 100\%$$

$$CH_4 \text{ Selectivity} = \frac{y_{CH_4}}{3y_{C_3H_6} + y_{CH_4} + y_{CO} + y_{CO_2}} * 100\%$$

$$C_3H_6 \text{ Yield} = \frac{\text{Conversion} * C_3H_6 \text{ Selectivity}}{100}$$

$$\text{Carbon balance} = \frac{3y_{C_3H_8} + 3y_{C_3H_6} + y_{CH_4} + y_{CO} + y_{CO_2}}{3y_{C_3H_8,0}} * 100\%$$

$$WHSV^{-1} = \frac{\text{Mass of the catalyst loaded}}{\text{Mass flow rate of the propane in feed gas}} [= ](kg_{C_3H_8}^{-1} kg_{catalyst} h)$$

where $y_i$ is the mole fraction of product i at the exit of the reactor. The term $y_{C3H8,0}$ is the mole fraction of propane in the feed gas. Selectivity and total balance are on a carbon basis.

Scanning Transmission Electron Microscopy (STEM)

STEM-ADF imaging was carried out in the Northwestern University Atomic and Nanoscale Characterization Experimental Center (NUANCE) with an aberration-corrected JEOL ARM-200F microscope at 200 kV. Meanwhile, energy-dispersive X-ray (EDX) spectra were also collected on the same equipment. Samples for STEM were dispersed in the acetone and dropped onto a TEM grid (Lacey carbon only, 300 mesh Cu). Then the TEM grid was heated at 100° C. for 15 min to remove solvent.

Diffuse Reflectance Infrared Fourier Transform Spectroscopy (DRIFTS)

Diffuse Reflectance Infrared Fourier Transform Spectroscopy (DRIFTS) was performed on a Thermo 6700 FTIR instrument equipped with a liquid nitrogen cooled MCT (mercury-cadmium-telluride) detector which allowed for measurement of IR spectra from 1000 to 4000 cm$^{-1}$, using pure argon (>99.9%, Airgas) as the carrier gas. Before CO adsorption, the sample was pretreated at the temperature of interest (e.g., 200° C.) for 30 min under nitrogen atmosphere, and then the gas was switched to 10% $O_2$/Ar for 30 min and to 10% $H_2$/Ar for another 30 min. The sample was then cooled to room temperature in the nitrogen atmosphere. After pretreatment, the feed gas was switched to 10% CO/$N_2$ for 30 min to saturate CO adsorption. The gas was switched to nitrogen purge for another 30 min to remove the gas phase CO and the spectra were recorded. Except for the pretreatment temperature, all spectra were collected using the same procedure and 128 scans with a resolution of 4 cm$^{-1}$.

Carbon Monoxide Pulse Chemisorption

CO pulse chemisorption was carried out on an AMI-200 instrument equipped with a Universal Gas Analyzer Mass Spectrometer (UGA-100). The sample was loaded into a U-type quartz tube, pretreated with 10% $O_2$/He at 200° C. for 1 hour, and then reduced in 10% $H_2$/$N_2$ at 200° C. for 1 hour. After reduction, the sample was cooled to 40° C. and CO pulse chemisorption was performed using 5% CO/He. Each gas pulse was 595 μL. Sample (Pt/$Al_2O_3$)@35c$In_2O_3$-450° C. was pretreated with 10% $O_2$/He at 250° C. for 1 hour, reduced in 10% $H_2$/$N_2$ at 200° C. for 1 hour, heated to 450° C. under He, and held for 1 hour at 450° C. Then, the sample was cooled to 40° C. where CO pulse chemisorption was performed.

Hydrogen Temperature Programmed Reduction ($H_2$-TPR) and Mass Spectroscopy

Hydrogen TPR ($H_2$-TPR) was performed on the AMI-200 instrument equipped with a Universal Gas Analyzer Mass Spectrometer (UGA-100). Samples were pretreated in reaction gas (10% propane and 5% $O_2$ with $N_2$ balance) at 450° C. for 2 hours, and then in 10% $O_2$/He at 250° C. for 1 hour with a flow rate of 100 sccm. After oxidation, the sample was purged with $N_2$ for 30 min at 250° C. and then cooled to 40° C. After gas stabilization at 40° C. for 2 hours, the sample was heated to 650° C. with a rate of 10° C./min in 10% $H_2$/$N_2$, and TCD signal was recorded. The outlet gas was also sampled by the UGA-100, and mass spectra were collected during the $H_2$-TPR process.

Other Techniques.

XPS (Thermo Scientific ESCALAB 250Xi) measurements were carried out in the Northwestern University Atomic and Nanoscale Characterization Experimental Center (NUANCE). The instrument was equipped with an electron flood gun and a scanning ion gun. X-ray absorption measurements at the Pt L3-edge were performed at sector 10 ID, Advance Photon Source (APS), Argonne National Laboratory, using a Si(111) double crystal monochromator. The ring energy of APS was 7 GeV. The samples were packed into self-supported wafers. All samples were measured in air at room temperature without pretreatment. Nitrogen physisorption was performed in a Micromeritics 3Flex BET instrument after degassing at 150° C. for 10 hours.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" can mean only one or can mean "one or more." Both embodiments are covered.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalent.

What is claimed is:

1. A catalyst comprising:
   a support having a surface;
   catalyst particles dispersed on the surface of the support, the catalyst particles comprising a material that is catalytically active for dehydrogenation of an alkane or an alcohol; and
   a catalytic porous overcoat on the catalyst particles, the porous overcoat comprising a material that is catalytically active for selective hydrogen combustion in the presence of the alkane or the alcohol, wherein the material that is catalytically active for selective hydrogen combustion is not a cobalt oxide or an iron oxide.

2. The catalyst of claim 1, wherein the catalyst particles comprise the material that is catalytically active for the dehydrogenation of the alkane.

3. The catalyst of claim 2, wherein the material that is catalytically active for the dehydrogenation of the alkane is platinum or a platinum alloy.

4. The catalyst of claim 1, wherein the material that is catalytically active for the selective hydrogen combustion is indium oxide, bismuth oxide, tungsten oxide, or a combination of two or more thereof.

5. The catalyst of claim 1, wherein the support comprises metal oxide particles.

6. The catalyst of claim 5, wherein the metal oxide is aluminum oxide.

7. The catalyst of claim 3, wherein the material that is catalytically active for the selective hydrogen combustion is indium oxide, bismuth oxide, tungsten oxide, or a combination of two or more thereof, and the support comprises aluminum oxide particles.

8. The catalyst of claim 7, wherein the catalytic porous overcoat has a thickness of 3 nm or less and the catalyst particles have an average diameter of 5 nm or less.

9. A method for the dehydrogenation of an alkane or an alcohol, the method comprising exposing the alkane or the alcohol to a catalyst in the presence of oxygen, the catalyst comprising:
   a support having a surface;
   catalyst particles dispersed on the surface of the support, the catalyst particles comprising a material that is catalytically active for the dehydrogenation of the alkane or the alcohol, wherein the material that is catalytically active for selective hydrogen combustion is not a cobalt oxide or an iron oxide; and
   a catalytic porous overcoat on the catalyst particles, the porous overcoat comprising a material that is catalytically active for selective hydrogen combustion in the presence of the alkane or the alcohol, whereby the alkane or the alcohol is dehydrogenated to form a dehydrogenation product.

10. The method of claim 9, wherein the alkane is exposed to the catalyst, the catalyst particles comprise the material that is catalytically active for the dehydrogenation of the alkane, and the dehydrogenation product is an alkene.

11. The method of claim 10, wherein alkane is propane and the dehydrogenation product is propylene.

12. The method of claim 9, wherein the alkane is exposed to the catalyst, the catalyst particles comprise the material that is catalytically active for the dehydrogenation of the alkane, and the dehydrogenation product is a cycloalkane.

13. The method of claim 9, wherein the alcohol is exposed to the catalyst, the catalyst particles comprise the material that is catalytically active for the dehydrogenation of the alcohol, and the dehydrogenation product is an aldehyde, a ketone, or an ester.

14. A method of making a catalyst, the method comprising:
   providing a support having a surface and a plurality of catalyst particles dispersed on the surface, the catalyst particles comprising a material that is catalytically active for the dehydrogenation of an alkane or an alcohol, wherein the material that is catalytically active for selective hydrogen combustion is not a cobalt oxide or an iron oxide; and
   overcoating the catalyst particles with a porous overcoat comprising a material that is catalytically active for selective hydrogen combustion in the presence of the alkane or the alcohol.

15. The method of claim 14, wherein providing the support having the surface and the plurality of catalyst particles dispersed on the surface comprises growing the catalyst particles on the support via atomic layer deposition.

16. The method of claim 15, wherein overcoating the catalyst particles with a porous overcoat comprises growing the porous overcoat on the catalyst particles via atomic layer deposition.

17. The catalyst of claim 4, wherein the material that is catalytically active for the selective hydrogen combustion is indium oxide.

18. The catalyst of claim 4, wherein the material that is catalytically active for the selective hydrogen combustion is bismuth oxide.

19. The catalyst of claim 4, wherein the material that is catalytically active for the selective hydrogen combustion is tungsten oxide.

20. The method of claim 9, wherein the material that is catalytically active for the selective hydrogen combustion is indium oxide.

21. The method of claim 9, wherein the method is carried out in a reactor and the step of exposing the alkane or the alcohol to a catalyst in the presence of oxygen comprising flowing the alkane or the alcohol and the oxygen into the chamber in a feed gas.

* * * * *

UNITED STATES PATENT AND TRADEMARK OFFICE
CERTIFICATE OF CORRECTION

| | |
|---|---|
| PATENT NO. | : 12,311,343 B2 |
| APPLICATION NO. | : 17/927200 |
| DATED | : May 27, 2025 |
| INVENTOR(S) | : Justin M. Notestein et al. |

Page 1 of 1

It is certified that error appears in the above-identified patent and that said Letters Patent is hereby corrected as shown below:

In the Claims

Claim 11, Column 16, Line 7:
Delete the phrase "wherein alkane is" and replace with --wherein the alkane is--.

Claim 21, Column 16, Line 52:
Delete the phrase "oxygen comprising" and replace with --oxygen comprises--.

Signed and Sealed this
First Day of July, 2025

Coke Morgan Stewart
*Acting Director of the United States Patent and Trademark Office*